(12) United States Patent
Tu et al.

(10) Patent No.: US 7,135,009 B2
(45) Date of Patent: Nov. 14, 2006

(54) GLAUCOMA STENT AND METHODS THEREOF FOR GLAUCOMA TREATMENT

(75) Inventors: Hosheng Tu, Newport Coast, CA (US); Gregory T. Smedley, Irvine, CA (US); David Haffner, Mission Viejo, CA (US); Barbara A. Niksch, Laguna Niguel, CA (US)

(73) Assignee: Glaukos Corporation, Laguna Hills, CA (US)

( * ) Notice: Subject to any disclaimer, the term of this patent is extended or adjusted under 35 U.S.C. 154(b) by 470 days.

(21) Appl. No.: 10/118,578

(22) Filed: Apr. 8, 2002

(65) Prior Publication Data
US 2002/0188308 A1  Dec. 12, 2002

Related U.S. Application Data

(60) Provisional application No. 60/281,973, filed on Apr. 7, 2001.

(51) Int. Cl.
*A61M 5/00* (2006.01)
*A61M 1/00* (2006.01)
*A61F 11/00* (2006.01)
*A61M 31/00* (2006.01)

(52) U.S. Cl. .................. 604/8; 604/9; 604/27; 606/108

(58) Field of Classification Search .............. 604/7–10, 604/290, 521, 48, 264, 117, 27–31, 43, 93.01, 604/289, 294, 298, 107, 131, 108, 35, 503, 604/505, 22; 606/108, 107, 109, 167, 170; 623/4.1, 6.12

See application file for complete search history.

(56) References Cited

U.S. PATENT DOCUMENTS 3,788,327 A    1/1974   Donowitz et al.
4,037,604 A    7/1977   Newkirk
4,168,697 A    9/1979   Cantekin
4,175,563 A    11/1979  Arenberg et al.
4,402,681 A    9/1983   Haas et al.
4,428,746 A    1/1984   Mendez
4,501,274 A    2/1985   Skjaerpe
4,521,210 A    6/1985   Wong (Continued)

FOREIGN PATENT DOCUMENTS

AU        200072059 A1    12/2000

(Continued)

OTHER PUBLICATIONS

Phillip C. Jacobi, MD, Thomas S. Dietlein, MD and Gunter K. Krieglstein, MD, Goniocurettage for Removing Trabecular Meshwork: Clinical Results of a new Surgical Technique in Advanced Cronic Open-Angle Glaucoma, *American Journal of Ophthalmology*, May 1999, pp. 505-510.

(Continued)

*Primary Examiner*—Patricia Bianco
*Assistant Examiner*—Leslie R. Deak
(74) *Attorney, Agent, or Firm*—Knobbe, Martens, Olson & Bear, LLP

(57) ABSTRACT

The invention relates generally to medical devices and methods for reducing the intraocular pressure in an animal eye and, more particularly, to stent type devices for permitting aqueous outflow from the eye's anterior chamber and associated methods thereof for the treatment of glaucoma. Some aspects provide a self-trephining glaucoma stent and methods thereof which advantageously allow for a "one-step" procedure in which the incision and placement of the stent are accomplished by a single device and operation. This desirably allows for a faster, safer, and less expensive surgical procedure.

10 Claims, 29 Drawing Sheets

U.S. PATENT DOCUMENTS

| | | | |
|---|---|---|---|
| 4,554,918 A | 11/1985 | White | |
| 4,604,087 A | 8/1986 | Joseph | |
| 4,632,842 A | 12/1986 | Karwoski et al. | |
| 4,634,418 A | 1/1987 | Binder | |
| 4,718,907 A | 1/1988 | Karwoski et al. | |
| 4,722,724 A | 2/1988 | Schocket | |
| 4,733,665 A | 3/1988 | Palmaz | |
| 4,750,901 A | 6/1988 | Molteno | |
| 4,846,172 A | 7/1989 | Berlin | |
| 4,886,488 A | 12/1989 | White | |
| 4,900,300 A | 2/1990 | Lee | |
| 4,936,825 A | 6/1990 | Ungerleider | |
| 4,946,436 A | 8/1990 | Smith | |
| 4,968,296 A | 11/1990 | Ritch et al. | |
| 5,041,081 A * | 8/1991 | Odrich | 604/9 |
| 5,092,837 A | 3/1992 | Ritch et al. | |
| 5,129,895 A | 7/1992 | Vassiliadis et al. | |
| 5,171,213 A | 12/1992 | Price, Jr. | |
| 5,178,604 A | 1/1993 | Baerveldt et al. | |
| 5,180,362 A | 1/1993 | Worst | |
| 5,207,685 A * | 5/1993 | Cinberg et al. | 606/109 |
| 5,246,451 A | 9/1993 | Trescony et al. | |
| 5,300,020 A | 4/1994 | L'Esperance, Jr. | |
| 5,338,291 A | 8/1994 | Speckman et al. | |
| 5,346,464 A | 9/1994 | Camras | |
| 5,360,399 A | 11/1994 | Stegmann | |
| 5,370,607 A | 12/1994 | Memmen | |
| 5,370,641 A | 12/1994 | O'Donnell, Jr. | |
| 5,372,577 A | 12/1994 | Ungerleider | |
| 5,397,300 A | 3/1995 | Baerveldt et al. | |
| 5,433,701 A * | 7/1995 | Rubinstein | 604/8 |
| 5,454,796 A | 10/1995 | Krupin | |
| 5,472,440 A | 12/1995 | Beckman | |
| 5,476,445 A | 12/1995 | Baerveldt et al. | |
| 5,486,165 A | 1/1996 | Stegmann | |
| 5,520,631 A | 5/1996 | Nordquist et al. | |
| 5,558,629 A | 9/1996 | Baerveldt et al. | |
| 5,558,630 A | 9/1996 | Fisher | |
| 5,562,641 A | 10/1996 | Flomenblit et al. | |
| RE35,390 E | 12/1996 | Smith | |
| 5,601,094 A | 2/1997 | Reiss | |
| 5,626,558 A | 5/1997 | Suson | |
| 5,626,559 A | 5/1997 | Solomon | |
| 5,639,278 A | 6/1997 | Dereume et al. | |
| 5,676,679 A | 10/1997 | Simon et al. | |
| 5,681,323 A | 10/1997 | Arick | |
| 5,702,419 A | 12/1997 | Berry et al. | |
| 5,704,907 A | 1/1998 | Nordquist et al. | |
| 5,741,333 A | 4/1998 | Frid | |
| 5,743,868 A | 4/1998 | Brown et al. | |
| 5,752,928 A | 5/1998 | de Roulhac et al. | |
| 5,807,302 A | 9/1998 | Wandel | |
| 5,810,870 A | 9/1998 | Myers et al. | |
| 5,830,139 A | 11/1998 | Abreu | |
| 5,865,831 A | 2/1999 | Cozean et al. | |
| 5,868,697 A | 2/1999 | Richter et al. | |
| 5,879,319 A | 3/1999 | Pynson et al. | |
| 5,882,327 A | 3/1999 | Jacob | |
| 5,893,837 A | 4/1999 | Eagles et al. | |
| 5,968,058 A | 10/1999 | Richter et al. | |
| 6,004,302 A | 12/1999 | Brierley | |
| 6,007,510 A | 12/1999 | Nigam | |
| 6,007,511 A | 12/1999 | Prywes | |
| 6,033,434 A | 3/2000 | Borghi | |
| 6,045,557 A | 4/2000 | White et al. | |
| 6,050,970 A | 4/2000 | Baerveldt | |
| 6,059,812 A | 5/2000 | Clerc et al. | |
| 6,071,286 A | 6/2000 | Mawad | |
| 6,174,305 B1 | 1/2001 | Mikus et al. | |
| 6,231,597 B1 | 5/2001 | Deem et al. | |
| 6,241,721 B1 | 6/2001 | Cozean et al. | |
| 6,375,642 B1 | 4/2002 | Grieshaber et al. | |
| 6,450,937 B1 | 9/2002 | Mercereau et al. | |
| 6,450,984 B1 | 9/2002 | Lynch et al. | |
| 6,464,724 B1 | 10/2002 | Lynch et al. | |
| 6,533,768 B1 | 3/2003 | Hill | |
| 6,544,249 B1 | 4/2003 | Yu et al. | |
| 6,595,945 B1 * | 7/2003 | Brown | 604/8 |
| 6,699,211 B1 | 3/2004 | Savage | |
| 6,736,791 B1 | 5/2004 | Tu et al. | |
| 2002/0013546 A1 | 1/2002 | Grieshaber et al. | |
| 2002/0026200 A1 | 2/2002 | Savage | |
| 2002/0072673 A1 | 6/2002 | Yamamoto et al. | |
| 2003/0069637 A1 | 4/2003 | Lynch et al. | |
| 2003/0088260 A1 | 5/2003 | Smedley et al. | |
| 2003/0236483 A1 | 12/2003 | Ren | |
| 2004/0254520 A1 | 12/2004 | Porteous et al. | |

FOREIGN PATENT DOCUMENTS

| | | |
|---|---|---|
| EP | 0 898 947 A2 | 3/1999 |
| EP | 1 114 627 A1 | 11/2001 |
| WO | WO 89/00869 | 2/1989 |
| WO | WO 92/19294 | 11/1992 |
| WO | WO 94/13234 | 6/1994 |
| WO | WO 98/30181 | 7/1998 |
| WO | WO 99/26567 | 6/1999 |
| WO | WO 99/30641 | 6/1999 |
| WO | WO 00/64389 | 11/2000 |
| WO | WO 00/64390 | 11/2000 |
| WO | WO 00/64391 | 11/2000 |
| WO | WO 00/64393 | 11/2000 |
| WO | WO/00/72788 A1 | 12/2000 |
| WO | WO/01/50943 A2 | 7/2001 |
| WO | WO 01/78631 A2 | 10/2001 |
| WO | WO 03/015659 A2 | 2/2003 |

OTHER PUBLICATIONS

Phillip C. Jacobi, MD, Thomas S. Dietlein, MD and Gunter K. Krieglstein, MD, Bimanual Trabecular Aspiration in *Pseudoexfoliation Glaucoma*, *Ophthalmology*, 1998, vol. 105, No. 5, May 1998, pp. 886-894.

Phillip C. Jacobi, MD, Thomas S. Dietlein, MD and Gunter K. Krieglstein, MD, Microendoscopic Trabecular Surgery in Glaucoma Management, *Ophthalmology*, 1999 vol. 106, No. 3, pp. 538-544.

Arthur L. Schwartz, MD, & Douglas R. Anderson, MD, Trabecular Surgery, *Arch Ophthalmol*, vol. 92, Aug. 1974, pp. 134-138.

R.A. Hill, Q. Ren, D.C. Nguyen, L.H. Liaw, & M.W. Berns, Free-Electron Laser (FEL) Ablation of Ocular Tissues, *Laser Med Sci 1998*, vol. 13, pp. 219-226.

Maurice H. Luntz, MD & D.G. Livingston, B.SC., Trabeculotomy AB Externo & Trabeculectomy in Congenital and Adult-Onset Glaucoma, *American Journal of Ophthalmology*, Feb. 1977, vol. 83, No. 2, pp. 174-179.

W.M. Grant, MD, Further Studies on Facility of Flow Through the Trabecular Meshwork, *AMA Archives of Ophthalmology*, Oct. 1958, vol. 60, pp. 523-533.

Richard A. Hill, MD, George Baerveldt, MD, Serdar A. Ozler, MD, Michael Pickford, BA, Glen A. Profeta, BS, & Micheal W. Berns, PhD, Laser Trabecular Ablation (LTA), *Laser in Surgery and Medicine*, 1991, vol. 11, pp. 341-346.

Detliev Spiegel, MD, Karin Kobuch, MD, Richard A. Hill, MD, Ronald L. Gross, MD, Schlemm's Canal Implant: A New Method to Lower Intraocular Pressure in Patients With POAG, *Opthalmic Surgery and Lasers*, Jun. 1999, vol. 30, No. 6, pp. 492-494.

L. Jay Katz, MD,, A Cell for Innovative Operations for Glaucoma, *Arch Ophthalmology*, Mar. 2000, vol. 118, pp. 412-413.

Anselm Kampik & Franz Grehn, Nutzen und Risiken Augenärzticher Therapie, *Hauptreferate der XXXIII, Essener Forbildung für Augenärzte*, Dec. 1998. (English translated version enclosed Benefits and Risks of Ophthalmological Therapy).

Detlev Spiegel, 7 Chirurgische Glaukomtherapie, pp. 79-88 (English translation enclosed).

* cited by examiner

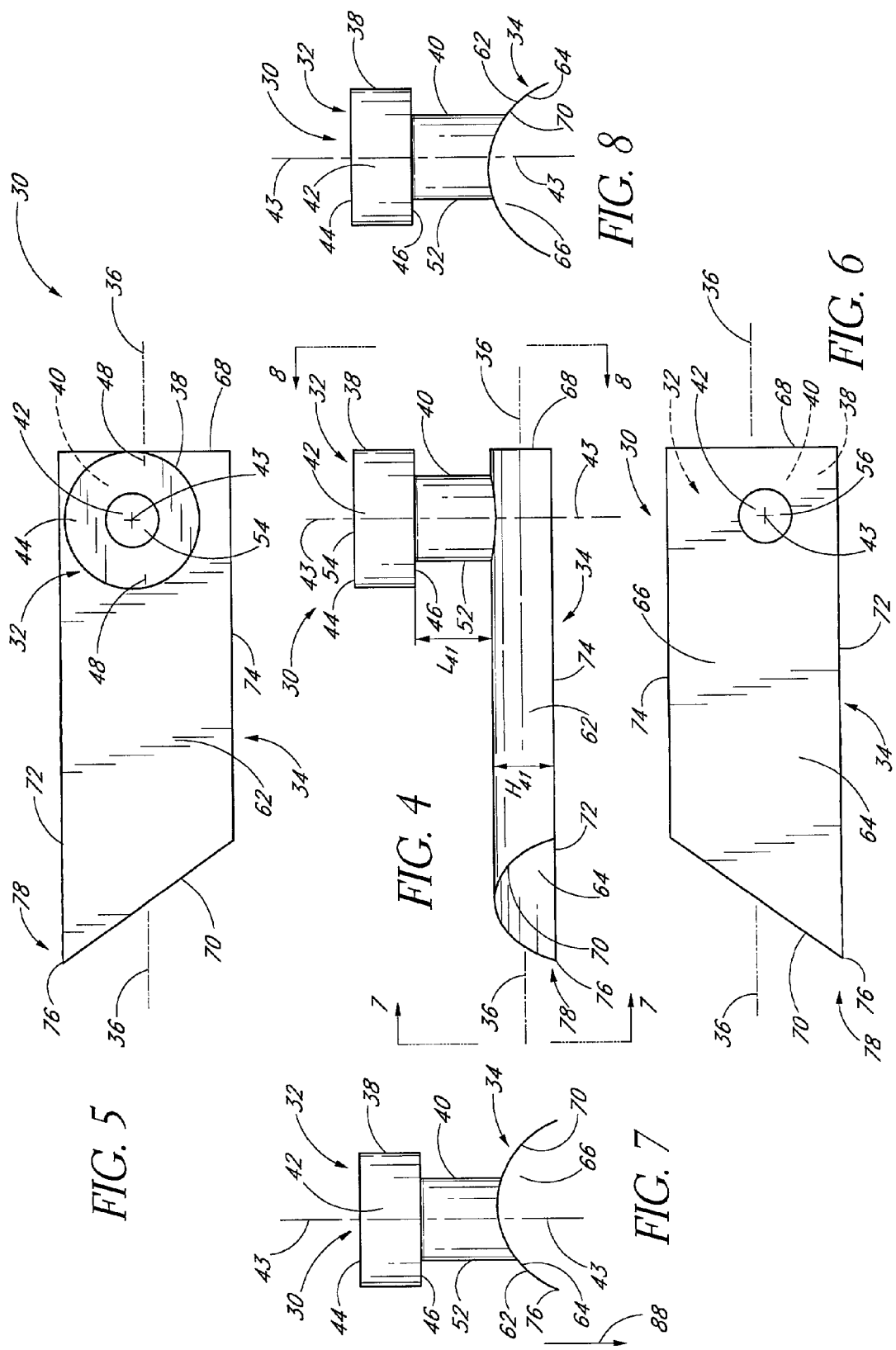

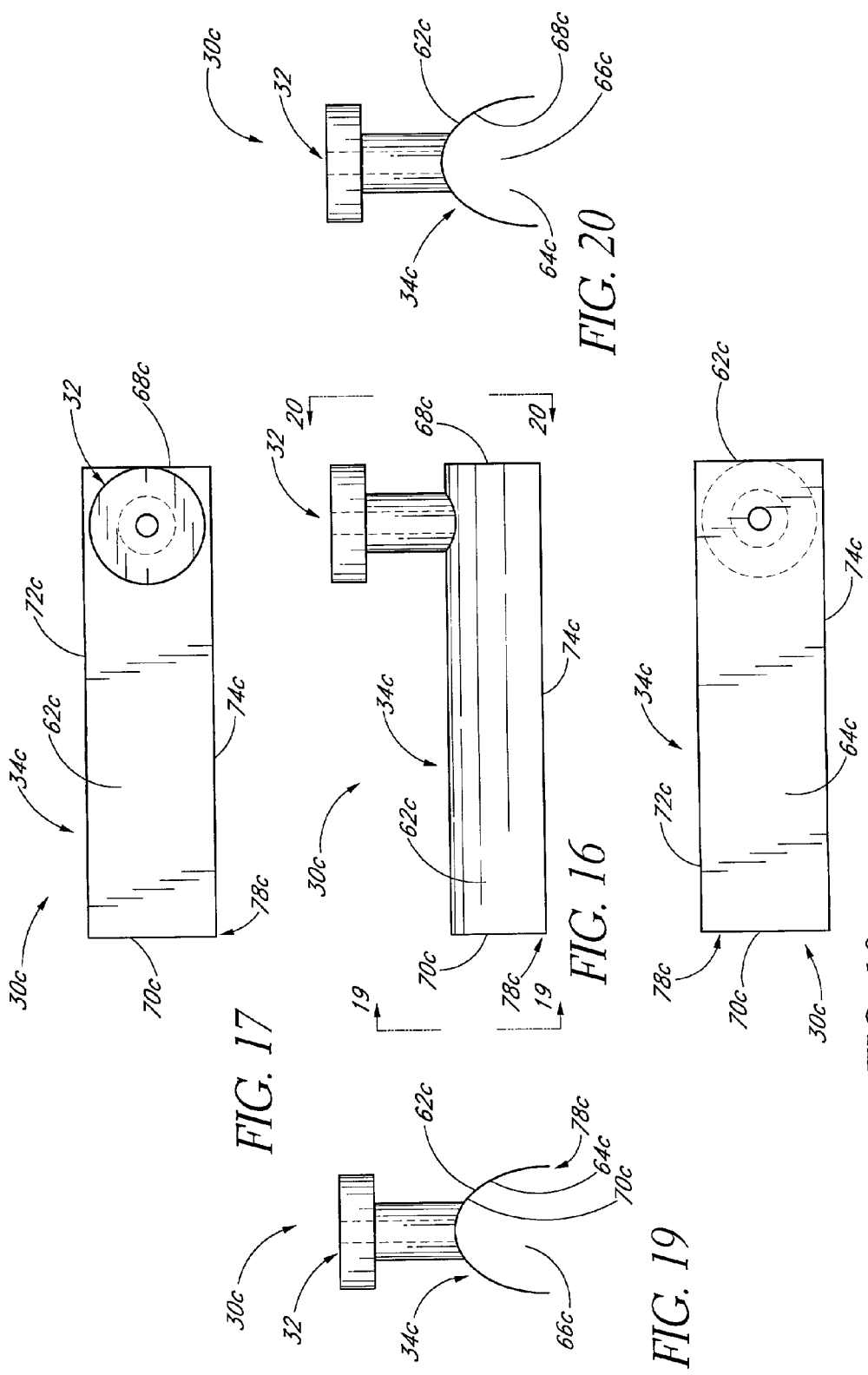

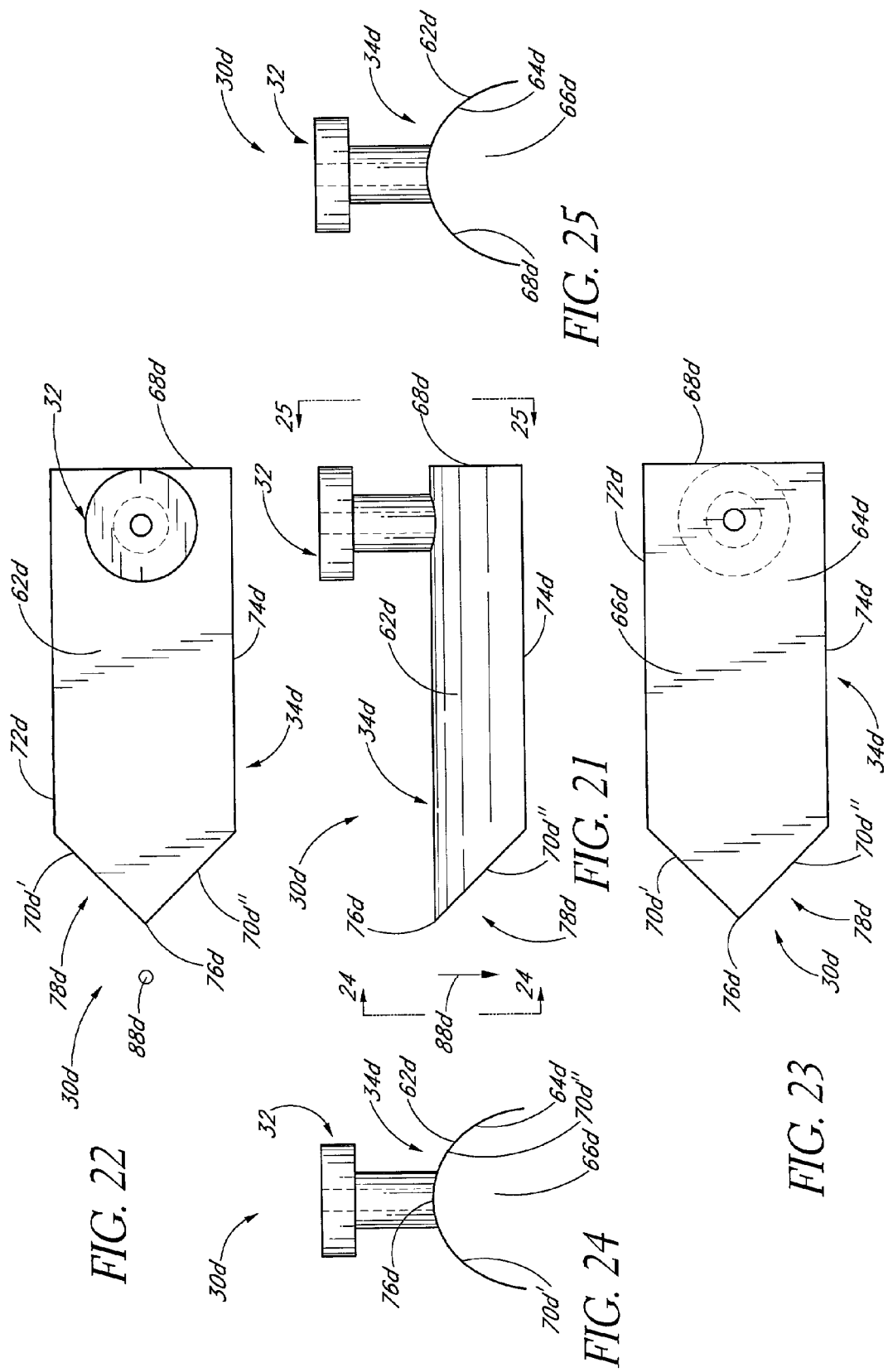

GLAUCOMA STENT AND METHODS THEREOF FOR GLAUCOMA TREATMENT

RELATED APPLICATIONS

This application claims priority to U.S. Provisional Application No. 60/281,973, filed Apr. 7, 2001, entitled GLAUCOMA SHUNT AND METHODS THEREOF FOR GLAUCOMA TREATMENT, the entire contents of which are hereby incorporated by reference herein.

BACKGROUND OF THE INVENTION

1. Field of the Invention

The invention relates generally to medical devices and methods for reducing the intraocular pressure in an animal eye and, more particularly, to shunt type devices for permitting aqueous outflow from the eye's anterior chamber and associated methods thereof for the treatment of glaucoma.

2. Description of the Related Art

The human eye is a specialized sensory organ capable of light reception and able to receive visual images. The trabecular meshwork serves as a drainage channel and is located in anterior chamber angle formed between the iris and the cornea. The trabecular meshwork maintains a balanced pressure in the anterior chamber of the eye by draining aqueous humor from the anterior chamber.

About two percent of people in the United States have glaucoma. Glaucoma is a group of eye diseases encompassing a broad spectrum of clinical presentations, etiologies, and treatment modalities. Glaucoma causes pathological changes in the optic nerve, visible on the optic disk, and it causes corresponding visual field loss, resulting in blindness if untreated. Lowering intraocular pressure is the major treatment goal in all glaucomas.

In glaucomas associated with an elevation in eye pressure (intraocular hypertension), the source of resistance to outflow is mainly in the trabecular meshwork. The tissue of the trabecular meshwork allows the aqueous humor ("aqueous") to enter Schlemm's canal, which then empties into aqueous collector channels in the posterior wall of Schlemm's canal and then into aqueous veins, which form the episcleral venous system. Aqueous humor is a transparent liquid that fills the region between the cornea, at the front of the eye, and the lens. The aqueous humor is continuously secreted by the ciliary body around the lens, so there is a constant flow of aqueous humor from the ciliary body to the eye's front chamber. The eye's pressure is determined by a balance between the production of aqueous and its exit through the trabecular meshwork (major route) or uveal scleral outflow (minor route). The trabecular meshwork is located between the outer rim of the iris and the back of the cornea, in the anterior chamber angle. The portion of the trabecular meshwork adjacent to Schlemm's canal (the juxtacanilicular meshwork) causes most of the resistance to aqueous outflow.

Glaucoma is grossly classified into two categories: closed-angle glaucoma, also known as angle closure glaucoma, and open-angle glaucoma. Closed-angle glaucoma is caused by closure of the anterior chamber angle by contact between the iris and the inner surface of the trabecular meshwork. Closure of this anatomical angle prevents normal drainage of aqueous humor from the anterior chamber of the eye.

Open-angle glaucoma is any glaucoma in which the angle of the anterior chamber remains open, but the exit of aqueous through the trabecular meshwork is diminished. The exact cause for diminished filtration is unknown for most cases of open-angle glaucoma. Primary open-angle glaucoma is the most common of the glaucomas, and it is often asymptomatic in the early to moderately advanced stage. Patients may suffer substantial, irreversible vision loss prior to diagnosis and treatment. However, there are secondary open-angle glaucomas which may include edema or swelling of the trabecular spaces (e.g., from corticosteroid use), abnormal pigment dispersion, or diseases such as hyperthyroidism that produce vascular congestion.

Current therapies for glaucoma are directed at decreasing intraocular pressure. Medical therapy includes topical ophthalmic drops or oral medications that reduce the production or increase the outflow of aqueous. However, these drug therapies for glaucoma are sometimes associated with significant side effects, such as headache, blurred vision, allergic reactions, death from cardiopulmonary complications, and potential interactions with other drugs. When drug therapy fails, surgical therapy is used. Surgical therapy for open-angle glaucoma consists of laser trabeculoplasty, trabeculectomy, and implantation of aqueous shunts after failure of trabeculectomy or if trabeculectomy is unlikely to succeed. Trabeculectomy is a major surgery that is widely used and is augmented with topically applied anticancer drugs, such as 5-flurouracil or mitomycin-C to decrease scarring and increase the likelihood of surgical success.

Approximately 100,000 trabeculectomies are performed on Medicare-age patients per year in the United States. This number would likely increase if the morbidity associated with trabeculectomy could be decreased. The current morbidity associated with trabeculectomy consists of failure (10–15%); infection (a life long risk of 2–5%); choroidal hemorrhage, a severe internal hemorrhage from low intraocular pressure, resulting in visual loss (1%); cataract formation; and hypotony maculopathy (potentially reversible visual loss from low intraocular pressure).

For these reasons, surgeons have tried for decades to develop a workable surgery for the trabecular meshwork.

The surgical techniques that have been tried and practiced are goniotomy/trabeculotomy and other mechanical disruptions of the trabecular meshwork, such as trabeculopuncture, goniophotoablation, laser trabecular ablation, and goniocurretage. These are all major operations and are briefly described below.

Goniotomy/Trabeculotomy: Goniotomy and trabeculotomy are simple and directed techniques of microsurgical dissection with mechanical disruption of the trabecular meshwork. These initially had early favorable responses in the treatment of open-angle glaucoma. However, long-term review of surgical results showed only limited success in adults. In retrospect, these procedures probably failed due to cellular repair and fibrosis mechanisms and a process of "filling in." Filling in is a detrimental effect of collapsing and closing in of the created opening in the trabecular meshwork. Once the created openings close, the pressure builds back up and the surgery fails.

Trabeculopuncture: Q-switched Neodynium (Nd) YAG lasers also have been investigated as an optically invasive technique for creating full-thickness holes in trabecular meshwork. However, the relatively small hole created by this trabeculopuncture technique exhibits a filling-in effect and fails.

Goniophotoablation/Laser Trabecular Ablation: Goniophotoablation is disclosed by Berlin in U.S. Pat. No. 4,846,172 and involves the use of an excimer laser to treat glaucoma by ablating the trabecular meshwork. This was demonstrated not to succeed by clinical trial. Hill et al. used an Erbium:YAG laser to create full-thickness holes through trabecular meshwork (Hill et al., Lasers in Surgery and Medicine 11:341–346, 1991). This technique was investigated in a primate model and a limited human clinical trial at the University of California, Irvine. Although morbidity was zero in both trials, success rates did not warrant further human trials. Failure was again from filling in of surgically created defects in the trabecular meshwork by repair mechanisms. Neither of these is a viable surgical technique for the treatment of glaucoma.

Goniocurretage: This is an ab interno (from the inside), mechanically disruptive technique that uses an instrument similar to a cyclodialysis spatula with a microcurrette at the tip. Initial results were similar to trabeculotomy: it failed due to repair mechanisms and a process of filling in.

Although trabeculectomy is the most commonly performed filtering surgery, viscocanulostomy (VC) and non-penetrating trabeculectomy (NPT) are two new variations of filtering surgery. These are ab externo (from the outside), major ocular procedures in which Schlemm's canal is surgically exposed by making a large and very deep scleral flap. In the VC procedure, Schlemm's canal is cannulated and viscoelastic substance injected (which dilates Schlemm's canal and the aqueous collector channels). In the NPT procedure, the inner wall of Schlemm's canal is stripped off after surgically exposing the canal.

Trabeculectomy, VC, and NPT involve the formation of an opening or hole under the conjunctiva and scleral flap into the anterior chamber, such that aqueous humor is drained onto the surface of the eye or into the tissues located within the lateral wall of the eye. These surgical operations are major procedures with significant ocular morbidity. When trabeculectomy, VC, and NPT are thought to have a low chance for success, a number of implantable drainage devices have been used to ensure that the desired filtration and outflow of aqueous humor through the surgical opening will continue. The risk of placing a glaucoma drainage device also includes hemorrhage, infection, and diplopia (double vision).

Examples of implantable shunts and surgical methods for maintaining an opening for the release of aqueous humor from the anterior chamber of the eye to the sclera or space beneath the conjunctiva have been disclosed in, for example, U.S. Pat. No. 6,059,772 to Hsia et al., and U.S. Pat. No. 6,050,970 to Baerveldt.

All of the above surgeries and variations thereof have numerous disadvantages and moderate success rates. They involve substantial trauma to the eye and require great surgical skill in creating a hole through the full thickness of the sclera into the subconjunctival space. The procedures are generally performed in an operating room and have a prolonged recovery time for vision.

The complications of existing filtration surgery have prompted ophthalmic surgeons to find other approaches to lowering intraocular pressure.

The trabecular meshwork and juxtacanilicular tissue together provide the majority of resistance to the outflow of aqueous and, as such, are logical targets for surgical removal in the treatment of open-angle glaucoma. In addition, minimal amounts of tissue are altered and existing physiologic outflow pathways are utilized.

As reported in Arch. Ophthalm. (2000) 118:412, glaucoma remains a leading cause of blindness, and filtration surgery remains an effective, important option in controlling the disease. However, modifying existing filtering surgery techniques in any profound way to increase their effectiveness appears to have reached a dead end. The article further states that the time has come to search for new surgical approaches that may provide better and safer care for patients with glaucoma.

Therefore, there is a great clinical need for a method of treating glaucoma that is faster, safer, and less expensive than currently available modalities.

SUMMARY OF THE INVENTION

The trabecular meshwork and juxtacanilicular tissue together provide the majority of resistance to the outflow of aqueous and, as such, are logical targets for surgical approach in the treatment of glaucoma. Various embodiments of glaucoma shunts are disclosed herein for aqueous to exit through the trabecular meshwork (major route) or uveal scleral outflow (minor route) or other route effective to reduce intraocular pressure (IOP).

Glaucoma surgical morbidity would greatly decrease if one were to bypass the focal resistance to outflow of aqueous only at the point of resistance, and to utilize remaining, healthy aqueous outflow mechanisms. This is in part because episcleral aqueous humor exerts a backpressure that prevents intraocular pressure from going too low, and one could thereby avoid hypotony. Thus, such a surgery would virtually eliminate the risk of hypotony-related maculopathy and choroidal hemorrhage. Furthermore, visual recovery would be very rapid, and the risk of infection would be very small, reflecting a reduction in incidence from 2–5% to about 0.05%.

Copending U.S. application Ser. No. 09/549,350, filed Apr. 14, 2000, entitled APPARATUS AND METHOD FOR TREATING GLAUCOMA, and copending U.S. application Ser. No. 09/704,276, filed Nov. 1, 2000, entitled GLAUCOMA TREATMENT DEVICE, disclose devices and methods of placing a trabecular shunt ab interno, i.e., from inside the anterior chamber through the trabecular meshwork, into Schlemm's canal. The entire contents of each one of these copending patent applications are hereby incorporated by reference herein. The invention encompasses both ab interno and ab externo glaucoma shunts or stents and methods thereof.

Techniques performed in accordance with aspects herein may be referred to generally as "trabecular bypass surgery." Advantages of this type of surgery include lowering intraocular pressure in a manner which is simple, effective, disease site-specific, and can potentially be performed on an outpatient basis.

Generally, trabecular bypass surgery (TBS) creates an opening, a slit, or a hole through trabecular meshwork with minor microsurgery. TBS has the advantage of a much lower risk of choroidal hemorrhage and infection than prior techniques, and it uses existing physiologic outflow mechanisms. In some aspects, this surgery can potentially be performed under topical or local anesthesia on an outpatient basis with rapid visual recovery. To prevent "filling in" of the hole, a biocompatible elongated device is placed within the hole and serves as a stent. U.S. patent application Ser. No. 09/549,350, filed Apr. 14, 2000, the entire contents of which are hereby incorporated by reference herein, discloses trabecular bypass surgery.

As described in U.S. patent application Ser. No. 09/549,350, filed Apr. 14, 2000, and U.S. application Ser. No. 09/704,276, filed Nov. 1, 2000, the entire contents each one of which are hereby incorporated by reference herein, a trabecular shunt or stent for transporting aqueous humor is provided. The trabecular stent includes a hollow, elongate tubular element, having an inlet section and an outlet section. The outlet section may optionally include two segments or elements, adapted to be positioned and stabilized inside Schlemm's canal. In one embodiment, the device appears as a "T" shaped device.

In one aspect of the invention, a delivery apparatus (or "applicator") is used for placing a trabecular stent through a trabecular meshwork of an eye. Certain embodiments of such a delivery apparatus are disclosed in copending U.S. application Ser. No. 10/101,548 (Inventors: Gregory T. Smedley, Irvine, Calif., Morteza Gharib, Pasadena, Calif., Hosheng Tu, Newport Beach, Calif.; ), filed Mar. 18, 2002, entitled APPLICATOR AND METHODS FOR PLACING A TRABECULAR SHUNT FOR GLAUCOMA TREATMENT, and U.S. Provisional Application No. 60/276,609, filed Mar. 16, 2001, entitled APPLICATOR AND METHODS FOR PLACING A TRABECULAR SHUNT FOR GLAUCOMA TREATMENT, the entire contents of each one of which are hereby incorporated by reference herein.

The stent has an inlet section and an outlet section. The delivery apparatus includes a handpiece, an elongate tip, a holder and an actuator. The handpiece has a distal end and a proximal end. The elongate tip is connected to the distal end of the handpiece. The elongate tip has a distal portion and is configured to be placed through a corneal incision and into an anterior chamber of the eye. The holder is attached to the distal portion of the elongate tip. The holder is configured to hold and release the inlet section of the trabecular stent. The actuator is on the handpiece and actuates the holder to release the inlet section of the trabecular stent from the holder. When the trabecular stent is deployed from the delivery apparatus into the eye, the outlet section is positioned in substantially opposite directions inside Schlemm's canal. In one embodiment, a deployment mechanism within the delivery apparatus includes a push-pull type plunger.

Some aspects of the invention relate to devices for reducing intraocular pressure by providing outflow of aqueous from an anterior chamber of an eye. The device generally comprises an elongated tubular member and cutting means. The tubular member is adapted for extending through a trabecular meshwork of the eye. The tubular member generally comprises a lumen having an inlet port and at least one outlet port for providing a flow pathway. The cutting means is mechanically connected to or is an integral part of the tubular member for creating an incision in the trabecular meshwork for receiving at least a portion of the tubular member.

In one aspect, a self-trephining glaucoma stent is provided for reducing and/or balancing intraocular pressure in an eye. The stent generally comprises a snorkel and a curved blade. The snorkel generally comprises an upper seat for stabilizing said stent within the eye, a shank and a lumen. The shank is mechanically connected to the seat and is adapted for extending through a trabecular meshwork of the eye. The lumen extends through the snorkel and has at least one inlet flow port and at least one outlet flow port. The blade is mechanically connected to the snorkel. The blade generally comprises a cutting tip proximate a distal-most point of the blade for making an incision in the trabecular meshwork for receiving the shank.

Some aspects of the invention relate to methods of implanting a trabecular stent device in an eye. In one aspect, the device has a snorkel mechanically connected to a blade. The blade is advanced through a trabecular meshwork of the eye to cut the trabecular meshwork and form an incision therein. At least a portion of the snorkel is inserted in the incision to implant the device in the eye.

Some aspects provide a self-trephining glaucoma stent and methods thereof which advantageously allow for a "one-step" procedure in which the incision and placement of the stent are accomplished by a single device and operation. This desirably allows for a faster, safer, and less expensive surgical procedure. In any of the embodiments, fiducial markings, indicia, or the like and/or positioning of the stent device in a preloaded applicator may be used for proper orientation and alignment of the device during implantation.

Among the advantages of trabecular bypass surgery is its simplicity. The microsurgery may potentially be performed on an outpatient basis with rapid visual recovery and greatly decreased morbidity. There is a lower risk of infection and choroidal hemorrhage, and there is a faster recovery, than with previous techniques.

For purposes of summarizing the invention, certain aspects, advantages and novel features of the invention have been described herein above. Of course, it is to be understood that not necessarily all such advantages may be achieved in accordance with any particular embodiment of the invention. Thus, the invention may be embodied or carried out in a manner that achieves or optimizes one advantage or group of advantages as taught or suggested herein without necessarily achieving other advantages as may be taught or suggested herein.

All of these embodiments are intended to be within the scope of the invention herein disclosed. These and other embodiments of the invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

Having thus summarized the general nature of the invention and some of its features and advantages, certain preferred embodiments and modifications thereof will become apparent to those skilled in the art from the detailed description herein having reference to the figures that follow, of which:

FIG. 4 is a side elevation view of the stent of FIG. 3;

FIG. 5 is a top plan view of the stent of FIG. 3;

FIG. 6 is a bottom plan view of the stent of FIG. 3;

FIG. 7 is a front end view of the stent of FIG. 3 (along line 7—7 of FIG. 4);

FIG. 8 is a rear end view of the stent of FIG. 3 (along line 8—8 of FIG. 4);

FIG. 16 is a side elevation view of a glaucoma stent having features and advantages in accordance with one embodiment of the invention;

FIG. 17 is a top plan view of the stent of FIG. 16;

FIG. 18 is a bottom plan view of the stent of FIG. 16;

FIG. 19 is a front end view along line 19—19 of FIG. 16;

FIG. 20 is a rear end view along line 20—20 of FIG. 16;

FIG. 21 is a side elevation view of a glaucoma stent having features and advantages in accordance with one embodiment of the invention;

FIG. 22 is a top plan view of the stent of FIG. 21;

FIG. 23 is a bottom plan view of the stent of FIG. 21;

FIG. 24 is a front end view along line 24—24 of FIG. 21;

FIG. 25 is a rear end view along line 25—25 of FIG. 21;

DETAILED DESCRIPTION OF THE PREFERRED EMBODIMENTS

The preferred embodiments of the invention described herein relate particularly to surgical and therapeutic treatment of glaucoma through reduction of intraocular pressure. While the description sets forth various embodiment specific details, it will be appreciated that the description is illustrative only and should not be construed in any way as limiting the invention. Furthermore, various applications of the invention, and modifications thereto, which may occur to those who are skilled in the art, are also encompassed by the general concepts described herein.

Figure 1:
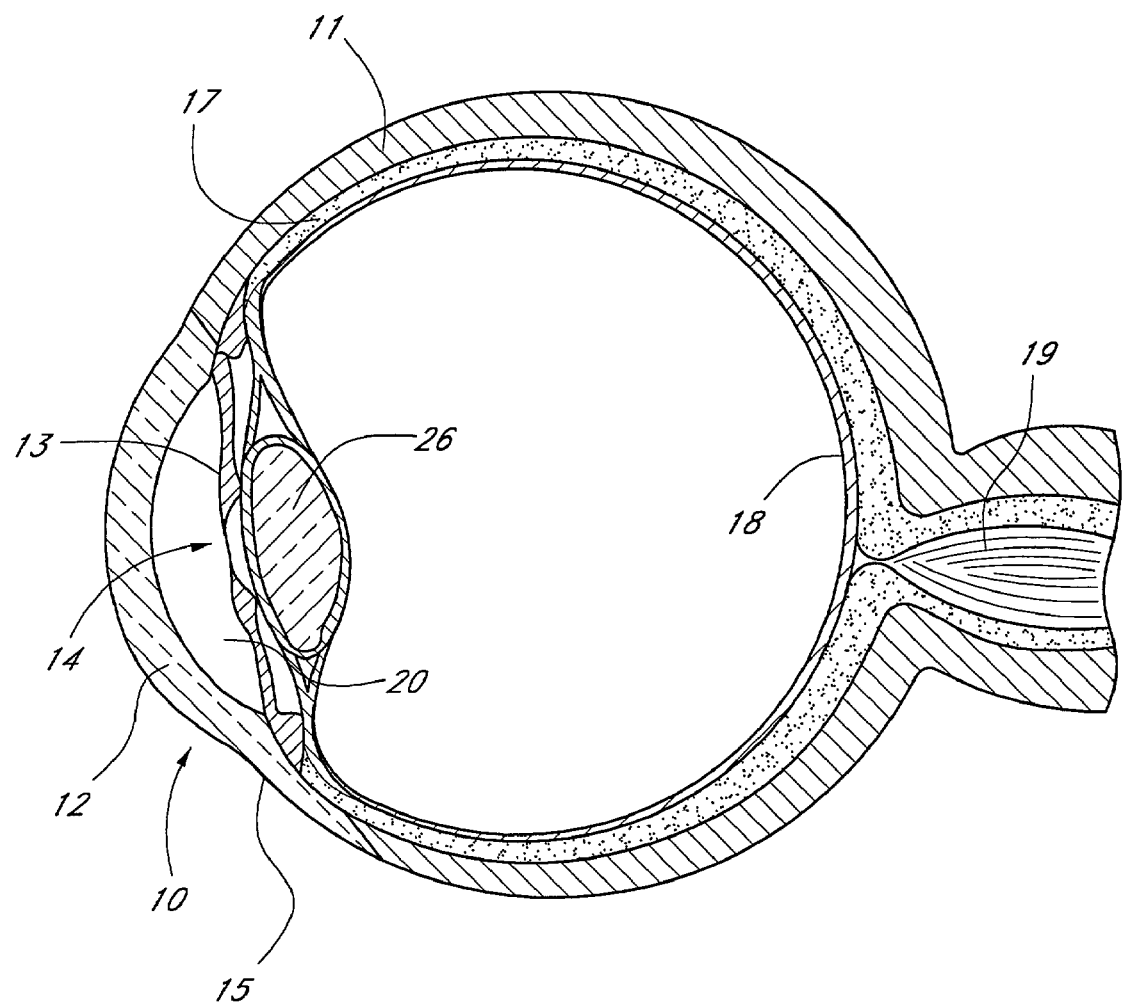
FIG. 1 is a coronal cross-sectional view of an eye.
Figure 2:
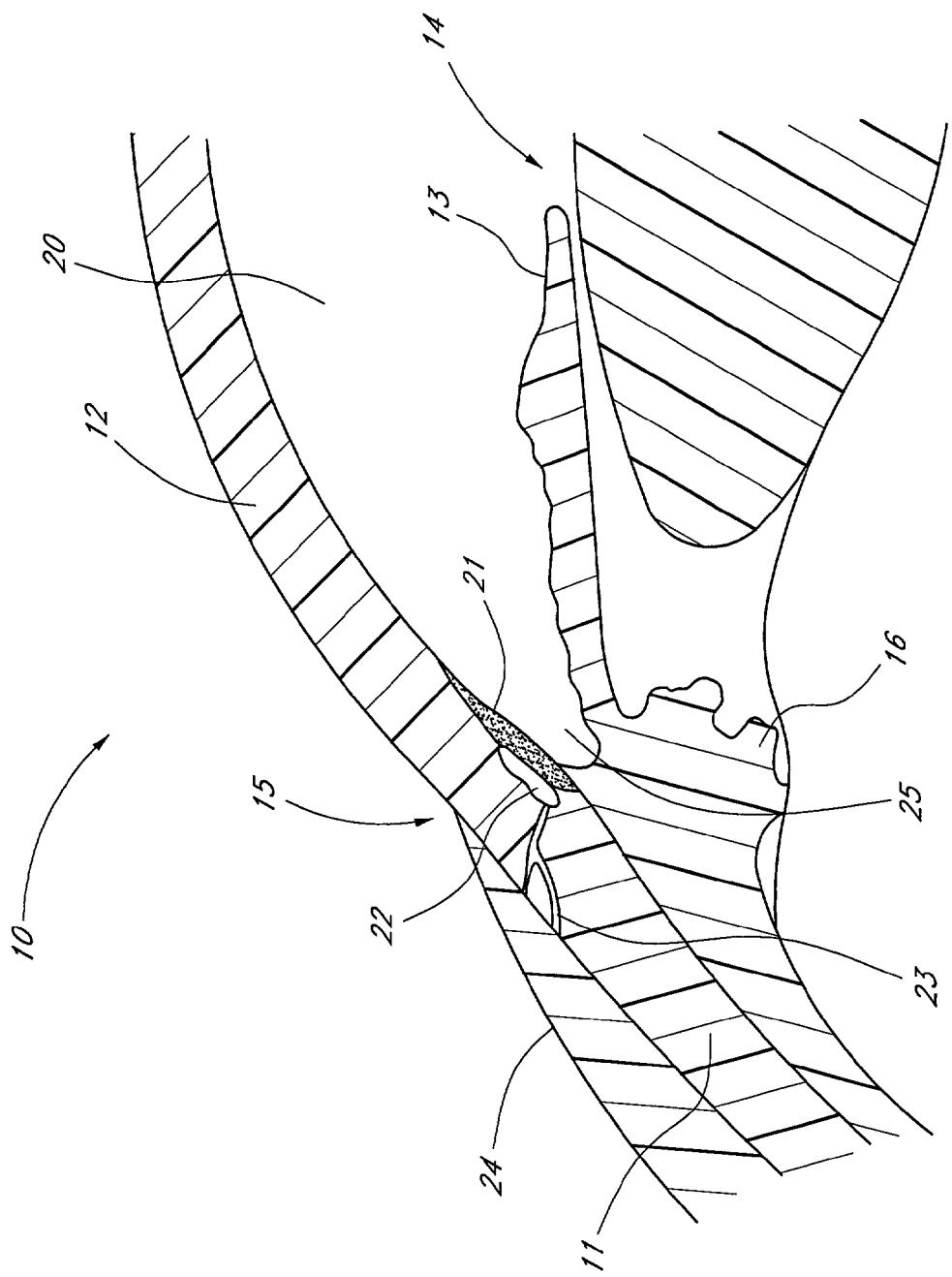
FIG. 2 is an enlarged cross-sectional view of an anterior chamber angle of the eye of FIG. 1.

FIG. 1 is a cross-sectional view of an eye 10, while FIG. 2 is a close-up view showing the relative anatomical locations of a trabecular meshwork 21, an anterior chamber 20, and Schlemm's canal 22. A sclera 11 is a thick collagenous tissue which covers the entire eye 10 except a portion which is covered by a cornea 12.

Referring to FIGS. 1 and 2, the cornea 12 is a thin transparent tissue that focuses and transmits light into the eye and through a pupil 14, which is a circular hole in the center of an iris 13 (colored portion of the eye). The cornea 12 merges into the sclera 11 at a juncture referred to as a limbus 15. A ciliary body 16 extends along the interior of the sclera 11 and is coextensive with a choroid 17. The choroid 17 is a vascular layer of the eye 10, located between the sclera 11 and a retina 18. An optic nerve 19 transmits visual information to the brain and is the anatomic structure that is progressively destroyed by glaucoma.

Still referring to FIGS. 1 and 2, the anterior chamber 20 of the eye 10, which is bound anteriorly by the cornea 12 and posteriorly by the iris 13 and a lens 26, is filled with aqueous humor (hereinafter referred to as "aqueous"). Aqueous is produced primarily by the ciliary body 16, then moves anteriorly through the pupil 14 and reaches an anterior chamber angle 25, formed between the iris 13 and the cornea 12.

As best illustrated by the drawing of FIG. 2, in a normal eye, aqueous is removed from the anterior chamber 20 through the trabecular meshwork 21. Aqueous passes through the trabecular meshwork 21 into Schlemm's canal 22 and thereafter through a plurality of aqueous veins 23, which merge with blood-carrying veins, and into systemic venous circulation. Intraocular pressure is maintained by an intricate balance between secretion and outflow of aqueous in the manner described above. Glaucoma is, in most cases, characterized by an excessive buildup of aqueous in the anterior chamber 20 which leads to an increase in intraocular pressure. Fluids are relatively incompressible, and thus intraocular pressure is distributed relatively uniformly throughout the eye 10.

As shown in FIG. 2, the trabecular meshwork 21 is adjacent a small portion of the sclera 11. Exterior to the sclera 11 is a conjunctiva 24. Traditional procedures that create a hole or opening for implanting a device through the tissues of the conjunctiva 24 and sclera 11 involve extensive surgery by an ab externo procedure, as compared to surgery for implanting a device, as described herein, which ultimately resides entirely within the confines of the sclera 11 and cornea 12.

Self-trephining Glaucoma Stent

Figure 3:
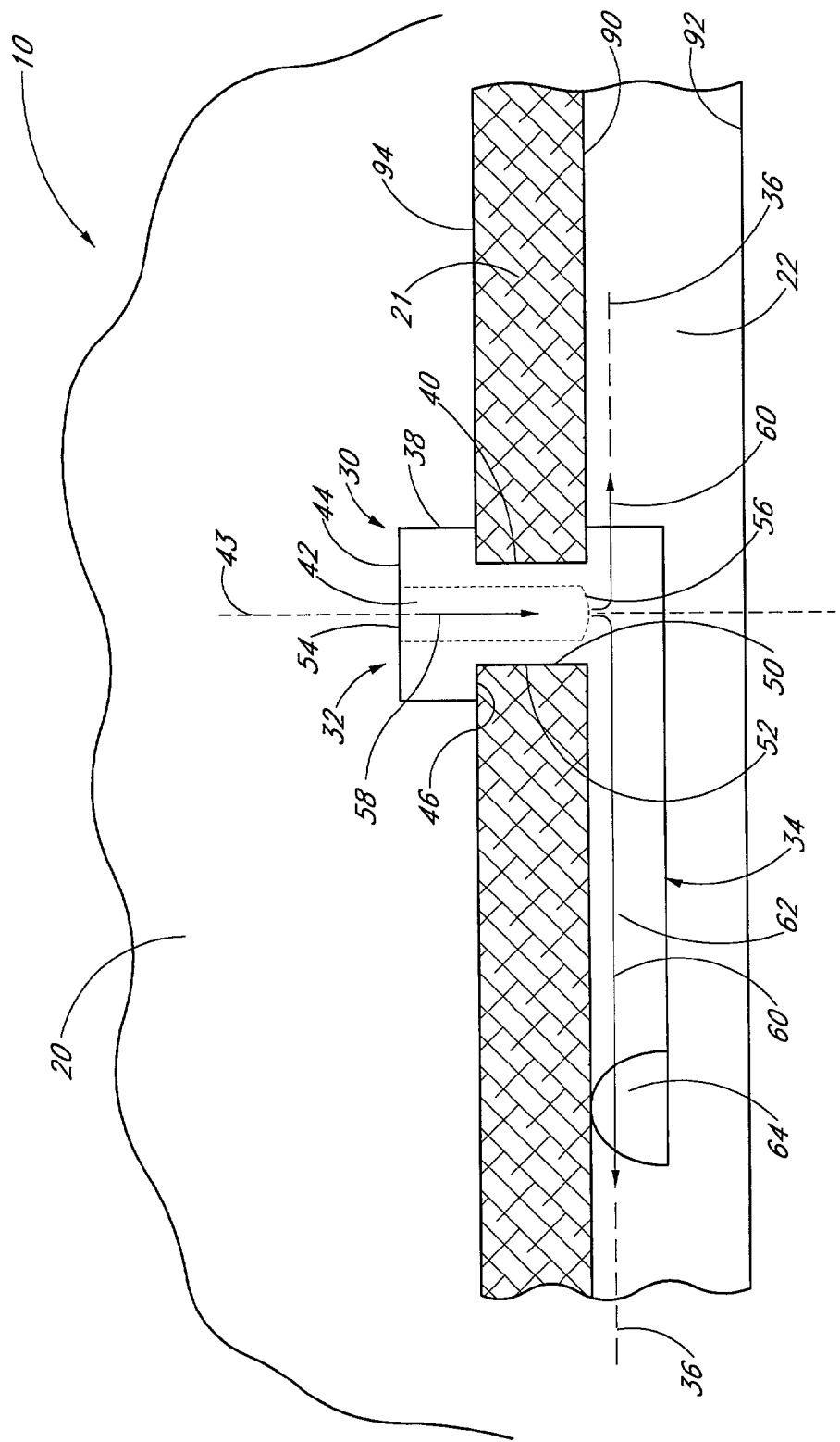
FIG. 3 is a simplified partial view of an eye illustrating the implantation of a glaucoma stent having features and advantages in accordance with one embodiment of the invention.

FIG. 3 generally illustrates the use of one embodiment of a trabecular stenting device 30 for establishing an outflow pathway, passing through the trabecular meshwork 21, which is discussed in greater detail below. FIGS. 4–9 are different views of the stent 30. Advantageously, and as discussed in further detail later herein, the self-trephining-stent allows a one-step procedure to make an incision in the trabecular mesh 21 and place the stent or implant 30 at the desired or predetermined position within the eye 10. Desirably, this facilitates and simplifies the overall surgical procedure.

In the illustrated embodiment of FIGS. 3–9, the shunt or stent 30 generally comprises a snorkel 32 and a main body portion or blade 34. The snorkel 32 and blade 34 are mechanically connected to or in mechanical communication with one another. The stent 30 and/or the body portion 34 have a generally longitudinal axis 36.

In the illustrated embodiment of FIGS. 3–9, the stent 30 comprises an integral unit. In modified embodiments, the stent 30 may comprise an assembly of individual pieces or components. For example, the stent 30 may comprise an assembly of the snorkel 32 and blade 34.

In the illustrated embodiment of FIGS. 3–9, the snorkel 32 is in the form of a generally elongate tubular member and generally comprises an upper seat, head or cap portion 38, a shank portion 40 and a lumen or passage 42 extending therethrough. The seat 38 is mechanically connected to or in mechanical communication with the shank 40 which is also mechanically connected to or in mechanical communication with the blade 34. The snorkel 32 and/or the lumen 42 have a generally longitudinal axis 43.

In the illustrated embodiment of FIGS. 3–9, the seat 38 is generally circular in shape and has an upper surface 44 and a lower surface 46 which, as shown in FIG. 3, abuts or rests against the trabecular meshwork 21 to stabilize the glaucoma stent 30 within the eye 10. In modified embodiments, the seat 38 may efficaciously be shaped in other suitable manners, as required or desired, giving due consideration to the goals of stabilizing the glaucoma stent 30 within the eye 10 and/or of achieving one or more of the benefits and advantages as taught or suggested herein. For example, the seat 38 may be shaped in other polygonal or non-polygonal shapes and/or comprise one or more ridges which extend radially outwards, among other suitable retention devices.

Figure 10:
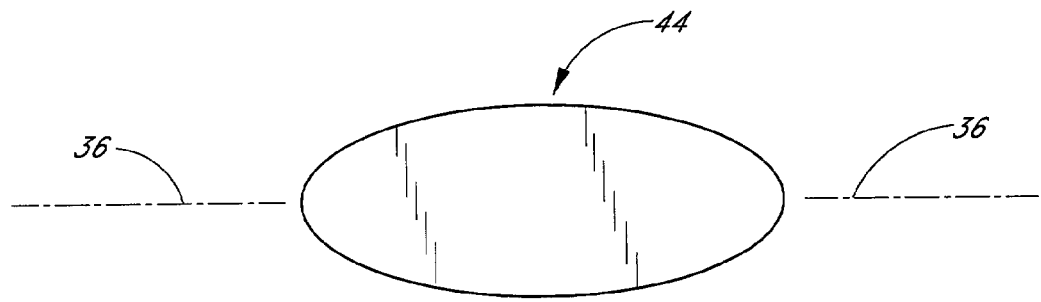
FIG. 10 is a top plan view of one exemplary embodiment of a snorkel top seating surface.
Figure 11:
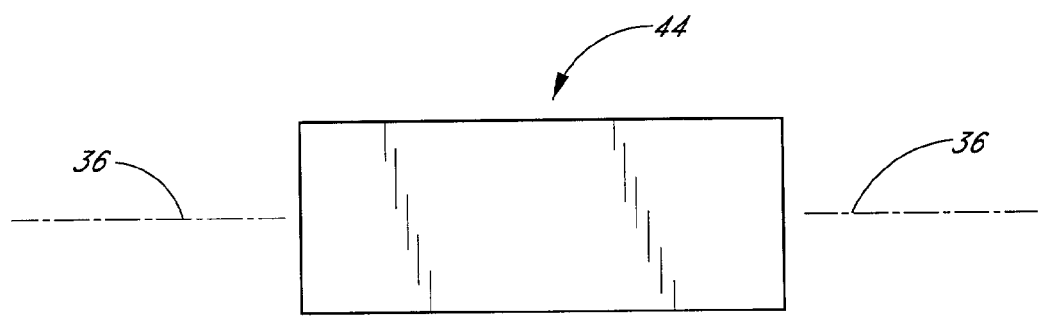
FIG. 11 is a top plan view of another exemplary embodiment of a snorkel top seating surface.
Figure 12:
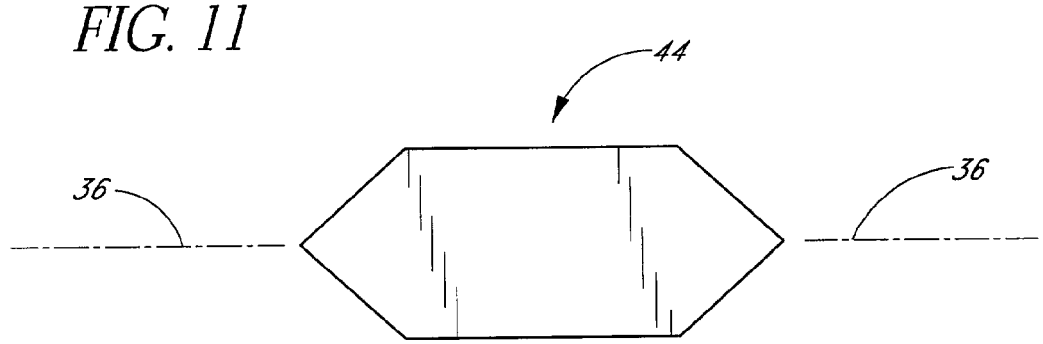
FIG. 12 is a top plan view of yet another exemplary embodiment of a snorkel top seating surface.
Figure 13:
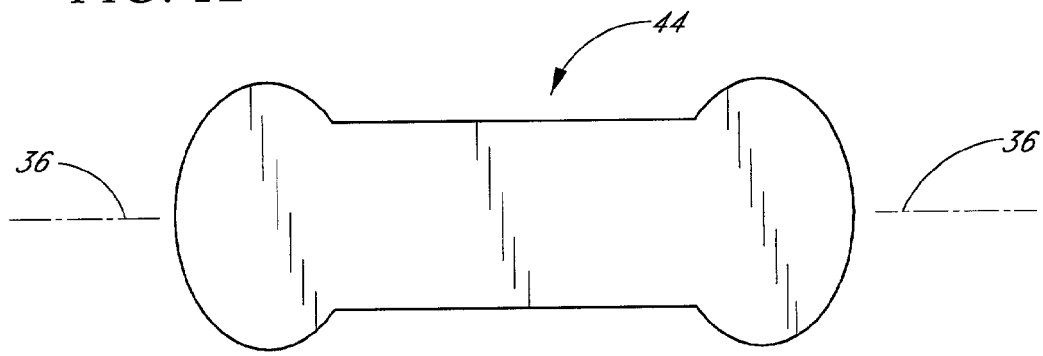
FIG. 13 is a top plan view of still another exemplary embodiment of a snorkel top seating surface.

In the illustrated embodiment of FIGS. 3–9, and as best seen in the top view of FIG. 5, the seat top surface 44 comprises fiducial marks or indicia 48. These marks or indicia 48 facilitate and ensure proper orientation and alignment of the stent 30 when implanted in the eye 10. The marks or indicia 48 may comprise visual differentiation means such as color contrast or be in the form of ribs, grooves, or the like. Alternatively, or in addition, the marks 48 may provide tactile sensory feedback to the surgeon by incorporating a radiopaque detectable or ultrasound imaginable substrate at about the mark 48. Also, the seat 38 and/or the seat top surface 44 may be configured in predetermined shapes aligned with the blade 34 and/or longitudinal axis 36 to provide for proper orientation of the stent device 30 within the eye 10. For example, the seat top surface 44 may be oval or ellipsoidal (FIG. 10), rectangular (FIG. 11), hexagonal (FIG. 12), among other suitable shapes (e.g. FIG. 13).

In the illustrated embodiment of FIGS. 3–9, and as indicated above, the seat bottom surface 46 abuts or rests against the trabecular meshwork 21 to stabilize and retain the glaucoma stent 30 within the eye 10. For stabilization purposes, the seat bottom surface 46 may comprise a stubbed surface, a ribbed surface, a surface with pillars, a textured surface, or the like.

In the illustrated embodiment of FIGS. 3–9, the snorkel shank 40 is generally cylindrical in shape. With the stent 30 implanted, as shown in FIG. 3, the shank 40 is generally positioned in an incision or cavity 50 formed in the trabecular meshwork 21 by the self-trephining stent 30. Advantageously, and as discussed further below, this single step of forming the cavity 50 by the stent 30 itself and placing the stent 30 in the desired position facilitates and expedites the overall surgical procedure. In modified embodiments, the snorkel shank 40 may efficaciously be shaped in other suitable manners, as required or desired. For example, the shank 40 may be in the shape of other polygonal or non-polygonal shapes, such as, oval, elliposoidal, and the like.

In the illustrated embodiment of FIGS. 3–9, and as best seen in FIG. 3, the shank 40 has an outer surface 52 in contact with the trabecular meshwork 21 surrounding the cavity 50. For stabilization purposes, the shank outer surface 52 may comprise a stubbed surface, a ribbed surface, a surface with pillars, a textured surface, or the like.

In the illustrated embodiment of FIGS. 3–9, the snorkel lumen 42 has an inlet port, opening or orifice 54 at the seat top surface 44 and an outlet port, opening or orifice 56 at the junction of the shank 40 and blade 34. The lumen 42 is generally cylindrical in shape, that is, it has a generally circular cross-section, and its ports 54, 56 are generally circular in shape. In modified embodiments, the lumen 42 and ports 54, 56 may be efficaciously shaped in other manners, as required or desired, giving due consideration to the goals of providing sufficient aqueous outflow and/or of achieving one or more of the benefits and advantages as taught or suggested herein. For example, the lumen 42 and/or one or both ports 54, 56 may be shaped in the form of ovals, ellipsoids, and the like, or the lumen 42 may have a tapered or stepped configuration.

Referring in particular to FIG. 3, aqueous from the anterior chamber 20 flows into the lumen 42 through the inlet port 54 (as generally indicated by arrow 58) and out of the outlet port 56 and into Schlemm's canal 22 (as generally indicated by arrows 60) to lower and/or balance the intraocular pressure (IOP). In another embodiment, as discussed in further detail below, one or more of the outlet ports may be configured to face in the general direction of the stent longitudinal axis 36. In modified embodiments, the snorkel 32 may comprise more than one lumen, as needed or desired, to facilitate multiple aqueous outflow transportation into Schlemm's canal 22.

In the illustrated embodiment of FIGS. 3–9, the blade longitudinal axis 36 and the snorkel longitudinal axis 43 are generally perpendicular to one another. Stated differently, the projections of the axes 36, 43 on a common plane which is not perpendicular to either of the axes 36, 43 intersect at 90°. The blade longitudinal axis 36 and the snorkel longitudinal axis 43 may intersect one another or may be offset from one another.

In the illustrated embodiment of FIGS. 3–9, the main body portion or blade 34 is a generally curved elongated sheet- or plate-like structure with an upper curved surface 62 and a lower curved surface 64 which defines a trough or open face channel 66. The perimeter of the blade 34 is generally defined by a curved proximal edge 68 proximate to the snorkel 32, a curved distal edge 70 spaced from the proximal edge 68 by a pair of generally straight lateral edges 72, 74 with the first lateral edge 72 extending beyond the second lateral edge 74 and intersecting with the distal edge 70 at a distal-most point 76 of the blade 34 proximate a blade cutting tip 78.

Figure 9:
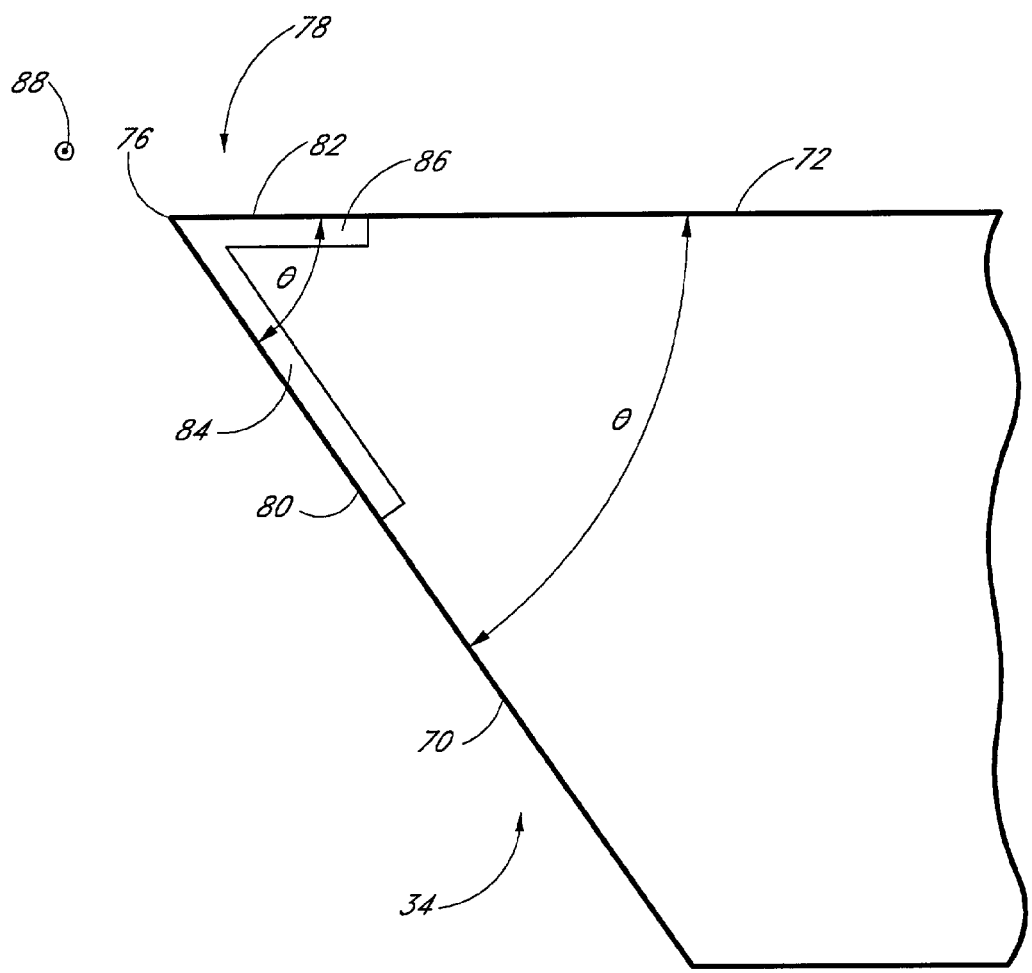
FIG. 9 is an enlarged top plan view of a cutting tip of the stent of FIG. 3.

In the illustrated embodiment of FIGS. 3–9, and as shown in the enlarged view of FIG. 9, the cutting tip 78 comprises a first cutting edge 80 on the distal edge 70 and a second cutting edge 82 on the lateral edge 72. The cutting edges 80, 82 preferably extend from the distal-most point 76 of the blade 34 and comprise at least a respective portion of the distal edge 70 and lateral edge 72. The respective cutting edges 80, 82 are formed at the sharp edges of respective beveled or tapered surfaces 84, 86. In one embodiment, the remainder of the distal edge 70 and lateral edge 72 are dull or rounded. In one embodiment, the tip 78 proximate to the distal-most end 76 is curved slightly inwards, as indicated generally by the arrow 88 in FIG. 5 and arrow 88 (pointed perpendicular and into the plane of the paper) in FIG. 9, relative to the adjacent curvature of the blade 34.

In modified embodiments, suitable cutting edges may be provided on selected portions of one or more selected blade edges 68, 70, 72, 74 with efficacy, as needed or desired, giving due consideration to the goals of providing suitable cutting means on the stent 30 for effectively cutting through the trabecular meshwork 21 (FIG. 3) and/or of achieving one or more of the benefits and advantages as taught or suggested herein.

Referring in particular to FIG. 9, in one embodiment, the ratio between the lengths of the cutting edges 80, 82 is about 2:1. In another embodiment, the ratio between the lengths of the cutting edges 80, 82 is about 1:1. In yet another embodiment, the ratio between the lengths of the cutting edges 80, 82 is about 1:2. In modified embodiments, the lengths of the cutting edges 80, 82 may be efficaciously selected in other manners, as required or desired, giving due consideration to the goals of providing suitable cutting means on the stent 30 for effectively cutting through the trabecular meshwork 21 (FIG. 3) and/or of achieving one or more of the benefits and advantages as taught or suggested herein.

Still referring in particular to FIG. 9, in one embodiment, the ratio between the lengths of the cutting edges 80, 82 is in the range from about 2:1 to about 1:2. In another embodiment, the ratio between the lengths of the cutting edges 80, 82 is in the range from about 5:1 to about 1:5. In yet another embodiment, the ratio between the lengths of the cutting edges 80, 82 is in the range from about 10:1 to about 1:10. In modified embodiments, the lengths of the cutting edges 80, 82 may be efficaciously selected in other manners, as required or desired, giving due consideration to the goals of providing suitable cutting means on the stent 30 for effectively cutting through the trabecular meshwork 21 (FIG. 3) and/or of achieving one or more of the benefits and advantages as taught or suggested herein.

As shown in the top view of FIG. 9, the cutting edge 80 (and/or the distal end 70) and the cutting edge 82 (and/or the lateral edge 72) intersect at an angle $\theta$. Stated differently, $\theta$ is the angle between the projections of the cutting edge 80 (and/or the distal end 70) and the cutting edge 82 (and/or the lateral edge 72) on a common plane which is not perpendicular to either of these edges.

Referring to in particular to FIG. 9, in one embodiment, the angle $\theta$ is about 50°. In another embodiment, the angle $\theta$ is in the range from about 40° to about 60°. In yet another embodiment, the angle $\theta$ is in the range from about 30° to about 70°. In modified embodiments, the angle $\theta$ may be efficaciously selected in other manners, as required or desired, giving due consideration to the goals of providing suitable cutting means on the stent 30 for effectively cutting through the trabecular meshwork 21 (FIG. 3) and/or of achieving one or more of the benefits and advantages as taught or suggested herein.

The stent 30 of the embodiments disclosed herein can be dimensioned in a wide variety of manners. Referring in particular to FIG. 3, the depth of Schlemm's canal 22 is typically about less than 400 microns (μm). Accordingly, the stunt blade 34 is dimensioned so that the height of the blade 34 (referred to as $H_{41}$ in FIG. 4) is typically less than about 400 μm. The snorkel shank 40 is dimensioned so that it has a length (referred to as $L_{41}$, in FIG. 4) typically in the range from about 150 μm to about 400 μm which is roughly the typical range of the thickness of the trabecular meshwork 21.

Of course, as the skilled artisan will appreciate, that with the stent 30 implanted, the blade 34 may rest at any suitable position within Schlemm's canal 22. For example, the blade 34 may be adjacent to a front wall 90 of Schlemm's canal 22 (as shown in FIG. 3), or adjacent to a back wall 92 of Schlemm's canal 22, or at some intermediate location therebetween, as needed or desired. Also, the snorkel shank 40 may extend into Schlemm's canal 22. The length of the snorkel shank 40 and/or the dimensions of the blade 34 may be efficaciously adjusted to achieve the desired implant positioning.

The trabecular stenting device 30 (FIGS. 3–9) of the exemplary embodiment may be manufactured or fabricated by a wide variety of techniques. These include, without limitation, by molding, thermo-forming, or other micromachining techniques, among other suitable techniques.

The trabecular stenting device 30 preferably comprises a biocompatible material such that inflammation arising due to irritation between the outer surface of the device 30 and the surrounding tissue is minimized. Biocompatible materials which may be used for the device 30 preferably include, but are not limited to, titanium, titanium alloys, medical grade silicone, e.g., Silastic™, available from Dow Corning Corporation of Midland, Mich.; and polyurethane, e.g., Pellethane™, also available from Dow Corning Corporation.

In other embodiments, the stent device 30 may comprise other types of biocompatible material, such as, by way of example, polyvinyl alcohol, polyvinyl pyrolidone, collagen, heparinized collagen, polytetrafluoroethylene, expanded polytetrafluoroethylene, fluorinated polymer, fluorinated elastomer, flexible fused silica, polyolefin, polyester, polysilicon, and/or a mixture of the aforementioned biocompatible materials, and the like. In still other embodiments, composite biocompatible material may be used, wherein a surface material may be used in addition to one or more of the aforementioned materials. For example, such a surface material may include polytetrafluoroethylene (PTFE) (such as Teflon™), polyimide, hydrogel, heparin, therapeutic drugs (such as beta-adrenergic antagonists and other antiglaucoma drugs, or antibiotics), and the like.

In an exemplary embodiment of the trabecular meshwork surgery, the patient is placed in the supine position, prepped, draped and anesthetized as necessary. In one embodiment, a small (less than about 1 mm) incision, which may be self sealing is made through the cornea 12. The corneal incision can be made in a number of ways, for example, by using a micro-knife, among other tools.

An applicator or delivery apparatus is used to advance the glaucoma stent 30 through the corneal incision and to the trabecular meshwork 21. Some embodiments of such a delivery apparatus are disclosed in copending U.S. application Ser. No. 10/101,548 (Inventors: Gregory T. Smedley, Irvine, Calif., Morteza Gharib, Pasadena, Calif., Hosheng Tu, Newport Beach, Calif., filed Mar. 18, 2002, entitled APPLICATOR AND METHODS FOR PLACING A TRABECULAR SHUNT FOR GLAUCOMA TREATMENT, and U.S. Provisional Application No. 60/276,609, filed Mar. 16, 2001, entitled APPLICATOR AND METHODS FOR PLACING A TRABECULAR SHUNT FOR GLAUCOMA TREATMENT, the entire contents of each one of which are hereby incorporated by reference herein. Some embodiments of a delivery apparatus are also discussed in further detail later herein. Gonioscopic, microscopic, or endoscopic guidance may be used during the trabecular meshwork surgery.

With the device 30 held by the delivery apparatus, the blade 34 of the self-trephining glaucoma stent device 30 is used to cut and/or displace the material of the trabecular meshwork 21. The snorkel shank 40 may also facilitate in removal of this material during implantation. The delivery apparatus is withdrawn once the device 30 has been implanted in the eye 10. As shown in FIG. 3, once proper implantation has been accomplished the snorkel seat 38 rests on a top surface 94 of the trabecular meshwork 21, the snorkel shank 40 extends through the cavity 50 (created by the device 30) in the trabecular meshwork 21, and the blade extends inside Schlemm's canal 22.

Advantageously, the embodiments of the self-trephining stent device of the invention allow for a "one-step" procedure to make an incision in the trabecular meshwork and to subsequently implant the stent in the proper orientation and alignment within the eye to allow outflow of aqueous from the anterior chamber through the stent and into Schlemm's canal to lower and/or balance the intraocular pressure (IOP). Desirably, this provides for a faster, safer, and less expensive surgical procedure.

Many complications can arise in trabecular meshwork surgeries, wherein a knife is first used to create an incision in the trabecular meshwork, followed by removal of the knife and subsequent installation of the stent. For instance, the knife may cause some bleeding which clouds up the surgical site. This may require more effort and time to clean the surgical site prior to placement of the stent. Moreover, this may cause the intraocular pressure (IOP) to rise or to fall undesireably. Thus, undesirably, such a multiple step procedure may demand crisis management which slows down the surgery, makes it less safe, and more expensive.

Figure 14:
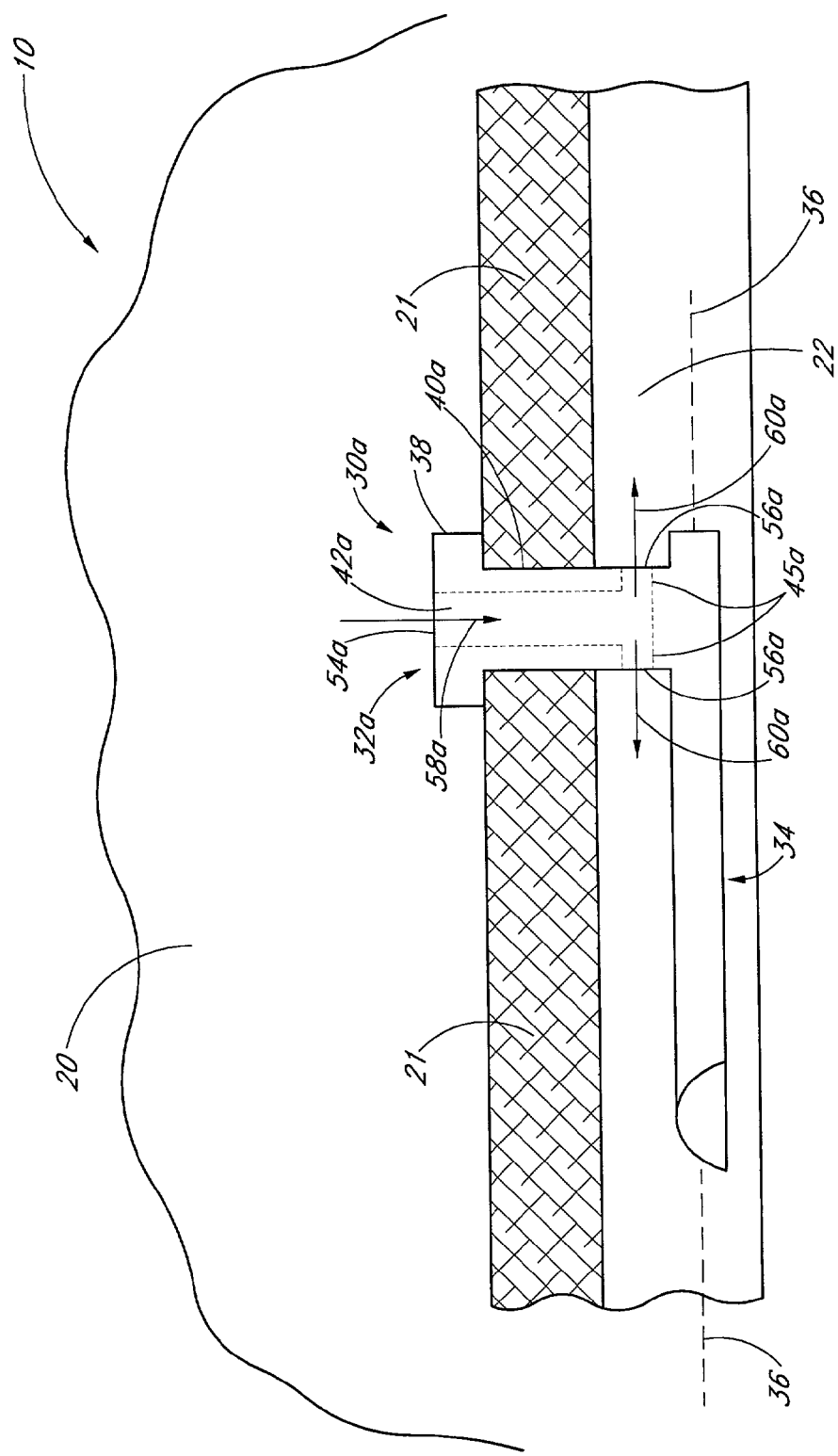
FIG. 14 is a simplified partial view of an eye illustrating the implantation of a glaucoma stent having features and advantages in accordance with another embodiment of the invention.

FIG. 14 is a simplified partial view of an eye 10 illustrating the implantation of a self-trephining glaucoma stent device 30a having features and advantages in accordance with one embodiment. The stent 30a is generally similar to the stent 30 of FIGS. 3–9 except that its snorkel 32a comprises a longer shank 40a which extends into Schlemm's canal 22 and a lumen 42a which bifurcates into two output channels 45a.

In the illustrated embodiment of FIG. 14, the shank 40a terminates at the blade 34. Aqueous flows from the anterior chamber 20 into the lumen 42a through an inlet port 54a (as generally indicated by arrow 58a). Aqueous then flows through the output channels 45a and out of respective outlet ports 56a and into Schlemm's canal 22 (as generally indicated by arrows 60a). The outlet channels 45a extend radially outwards in generally opposed directions and the outlet ports 56a are configured to face in the general direction of the stent longitudinal axis 36 so that they open into Schlemm's canal 22 and are in proper orientation to allow aqueous outflow into Schlemm's canal 22 for lowering and/or balancing the intraocular pressure (IOP). As indicated above, fiducial marks or indicia and/or predetermined shapes of the snorkel seat 38 allow for proper orientation of the blade 34 and also the output channels 45a and respective ports 56a within Schlemm's canal.

In the illustrated embodiment of FIG. 14, two outflow channels 45a are provided. In another embodiment, only one outflow channel 45a is provided. In yet another embodiment, more than two outflow channels 45a are provided. In modified embodiments, the lumen 42a may extend all the way through to the blade 34 and provide an outlet port as discussed above with reference to the embodiment of FIGS. 3–9.

Figure 15:
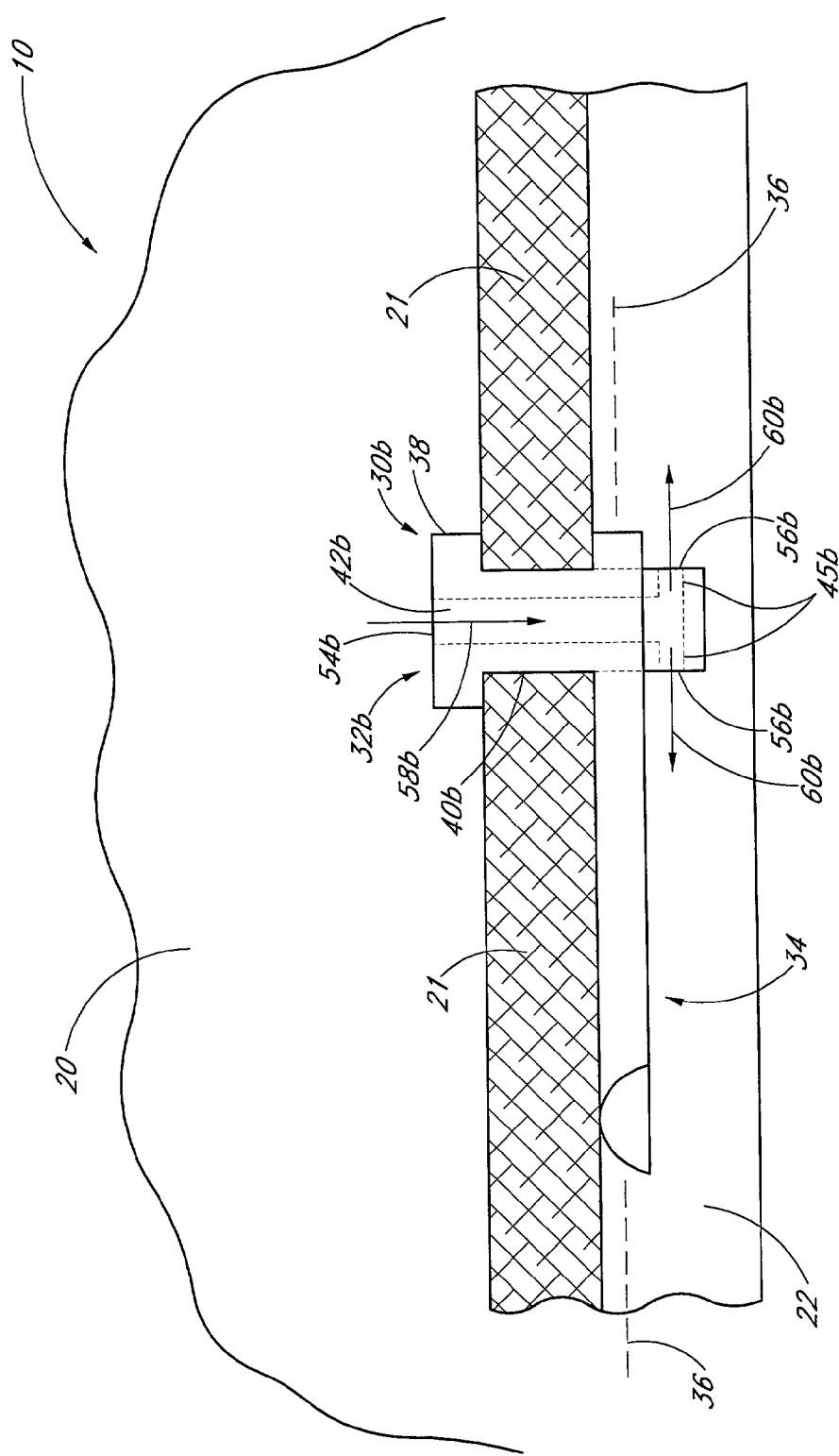
FIG. 15 is a simplified partial view of an eye illustrating the implantation of a glaucoma stent having features and advantages in accordance with a further embodiment of the invention.

FIG. 15 is a simplified partial view of an eye 10 illustrating the implantation of a self-trephining glaucoma stent device 30b having features and advantages in accordance with one embodiment. The stent 30b is generally similar to the stent 30 of FIGS. 3–9 except that its snorkel 32b comprises a longer shank 40b which extends into Schlemm's canal 22 and a lumen 42b which bifurcates into two output channels 45b.

In the illustrated embodiment of FIG. 15, the shank 40b extends through the blade 34. Aqueous flows from the anterior chamber 20 into the lumen 42b through an inlet port 54b (as generally indicated by arrow 58b). Aqueous then flows through the output channels 45b and out of respective outlet ports 56b and into Schlemm's canal 22 (as generally indicated by arrows 60b). The outlet channels 45b extend radially outwards in generally opposed directions and the outlet ports 56b are configured to face in the general direction of the stent longitudinal axis 36 so that they open into Schlemm's canal 22 and are in proper orientation to allow aqueous outflow into Schlemm's canal 22 for lowering and/or balancing the intraocular pressure (IOP). As indicated above, fiducial marks or indicia and/or predetermined shapes of the snorkel seat 38 allow for proper orientation of the blade 34 and also the output channels 45b and respective ports 56b within Schlemm's canal.

In the illustrated embodiment of FIG. 15, two outflow channels 45b are provided. In another embodiment, only one outflow channel 45b is provided. In yet another embodiment, more than two outflow channels 45b are provided. In modified embodiments, the lumen 42b may extend all the way through to the blade 34 and provide an outlet port as discussed above with reference to the embodiment of FIGS. 3–9.

FIGS. 16–20 show different views of a self-trephining glaucoma stent device 30c having features and advantages in accordance with one embodiment. The stent 30c is generally similar to the stent 30 of FIGS. 3–9 except that it has a modified blade configuration. The stent 30c comprises a blade 34c which is a generally curved elongated sheet- or plate-like structure with an upper curved surface 62c and a lower curved surface 64c which defines a trough or open face channel 66c. The perimeter of the blade 34c is generally defined by a curved proximal edge 68c proximate to the snorkel 32, a curved distal edge 70c spaced from the proximal edge 68c by a pair of generally straight lateral edges 72c, 74c which are generally parallel to one another and have about the same length.

In the illustrated embodiment of FIGS. 16–20, the blade 34c comprises a cutting tip 78c. The cutting tip 78c preferably includes cutting edges formed on selected portions of the distal edge 70c and adjacent portions of the lateral edges 72c, 74c for cutting through the trabecular meshwork for placement of the snorkel 32. The cutting edges are sharp edges of beveled or tapered surfaces as discussed above in reference to FIG. 9. The embodiment of FIGS. 16–20 may be efficaciously modified to incorporate the snorkel configuration of the embodiments of FIGS. 14 and 15.

FIGS. 21–25 show different views of a self-trephining glaucoma stent device 30d having features and advantages in accordance with one embodiment. The stent 30d is generally similar to the stent 30 of FIGS. 3–9 except that it has a modified blade configuration. The stent 30d comprises a blade 34d which is a generally curved elongated sheet- or plate-like structure with an upper curved surface 62d and a lower curved surface 64d which defines a trough or open face channel 66d. The perimeter of the blade 34d is generally defined by a curved proximal edge 68d proximate to the snorkel 32, a pair of inwardly converging curved distal edges 70d', 70d" spaced from the proximal edge 68d by a pair of generally straight respective lateral edges 72d, 74d which are generally parallel to one another and have about the same length. The distal edges 70d', 70d" intersect at a distal-most point 76d of the blade 34d proximate a blade cutting tip 78d.

In the illustrated embodiment of FIGS. 21–25, the cutting tip 78d preferably includes cutting edges formed on the distal edges 70d', 70d" and extending from the distal-most point 76d of the blade 34d. In one embodiment, the cutting edges extend along only a portion of respective distal edges 70d', 70d". In another embodiment, the cutting edges extend along substantially the entire length of respective distal edges 70d', 70d". In yet another embodiment, at least portions of the lateral edges 72d, 74d proximate to respective distal edges 70d', 70d" have cutting edges. In a further embodiment, the tip 78d proximate to the distal-most end 76d is curved slightly inwards, as indicated generally by the arrow 88d in FIG. 21 and arrow 88d (pointed perpendicular and into the plane of the paper) in FIG. 22, relative to the adjacent curvature of the blade 34d.

In the embodiment of FIGS. 21–25, the cutting edges are sharp edges of beveled or tapered surfaces as discussed above in reference to FIG. 9. The embodiment of FIGS. 21–25 may be efficaciously modified to incorporate the snorkel configuration of the embodiments of FIGS. 14 and 15.

Figure 28:
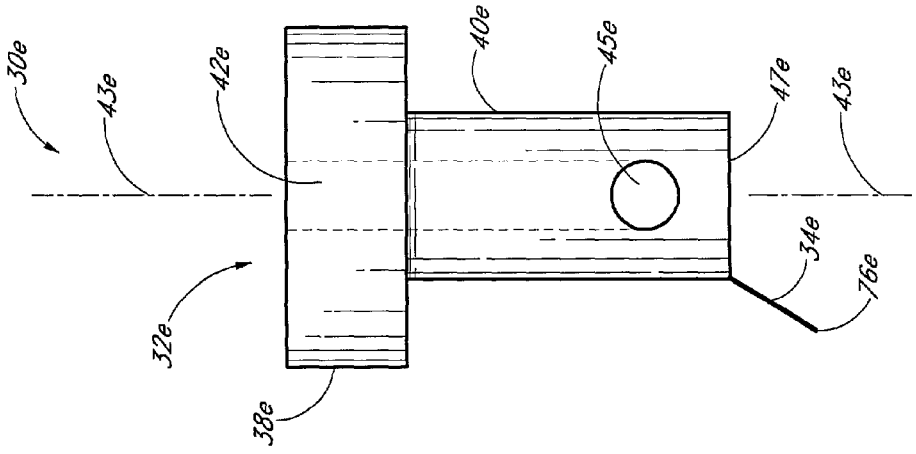
FIG. 28 is a rear end view along line 28—28 of FIG. 26.
Figure 26:
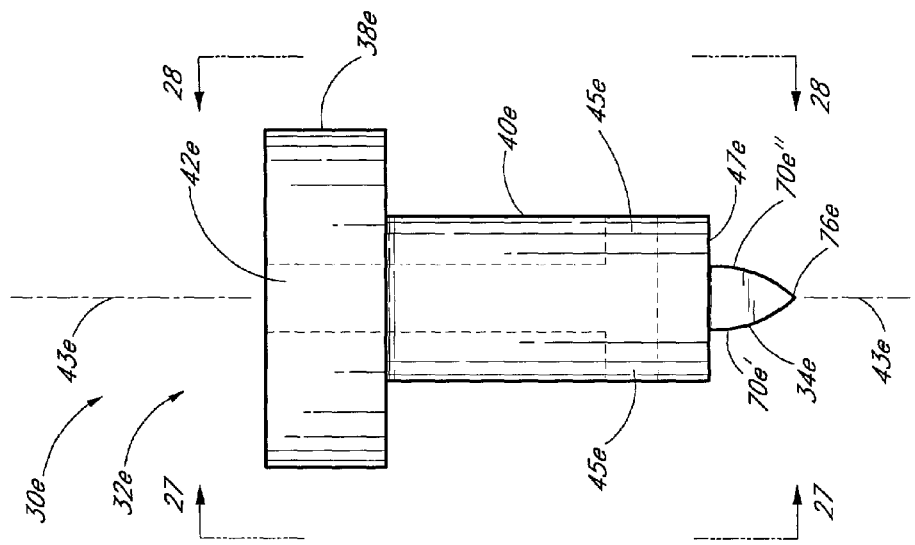
FIG. 26 is a front elevation view of a glaucoma stent having features and advantages in accordance with one embodiment of the invention.
Figure 27:
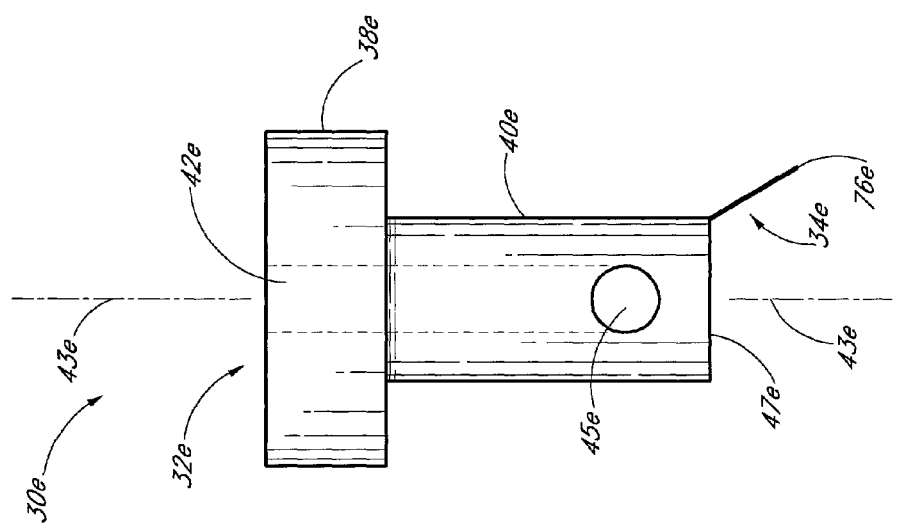
FIG. 27 is a side elevation view along line 27—27 of FIG. 26.

FIGS. 26–28 show different views of a self-trephining glaucoma stent device 30e having features and advantages in accordance with one embodiment. The stent device 30e generally comprises a snorkel 32e mechanically connected to or in mechanical communication with a blade or cutting tip 34e. The snorkel 32e has a seat, head or cap portion 38e mechanically connected to or in mechanical communication with a shank 40e, as discussed above. The shank 40e has a distal end or base 47e. The snorkel 32e further has a lumen 42e which bifurcates into a pair of outlet channels 45e, as discussed above in connection with FIGS. 14 and 15. Other lumen and inlet and outlet port configurations as taught or suggested herein may also be efficaciously used, as needed or desired.

In the illustrated embodiment of FIGS. 26–28, the blade 34e extends downwardly and outwardly from the shank distal end 47e. The blade 34e is angled relative to a generally longitudinal axis 43e of the snorkel 32e, as best seen in FIGS. 27 and 28. The blade 34e has a distal-most point 76e. The blade or cutting tip 34e has a pair of side edges 70e', 70e", including cutting edges, terminating at the distal-most point 76e, as best seen in FIG. 26. In one embodiment, the cutting edges are sharp edges of beveled or tapered surfaces as discussed above in reference to FIG. 9.

Referring to FIGS. 26–28, in one embodiment, the blade 34e includes cutting edges formed on the edges 70e', 70e" and extending from the distal-most point 76e of the blade 34d. In one embodiment, the cutting edges extend along only a portion of respective distal edges 70e', 70e". In another embodiment, the cutting edges extend along substantially the entire length of respective distal edges 70e', 70e". In yet another embodiment, the blade or cutting tip 34e comprises a bent tip of needle, for example, a 30 gauge needle.

In general, any of the blade configurations disclosed herein may be used in conjunction with any of the snorkel configurations disclosed herein or incorporated by reference herein to provide a self-trephining glaucoma stent device for making an incision in the trabecular meshwork for receiving the corresponding snorkel to provide a pathway for aqueous outflow from the eye anterior chamber to Schlemm's canal, thereby effectively lowering and/or balancing the intraocular pressure (IOP). The self-trephining ability of the device, advantageously, allows for a "one-step" procedure in which the incision and placement of the snorkel are accomplished by a single device and operation. In any of the embodiments, fiducial markings or indicia, and/or preselected configuration of the snorkel seat, and/or positioning of the stent device in a preloaded applicator may be used for proper orientation and alignment of the device during implantation.

Delivery Apparatus

Figure 29:
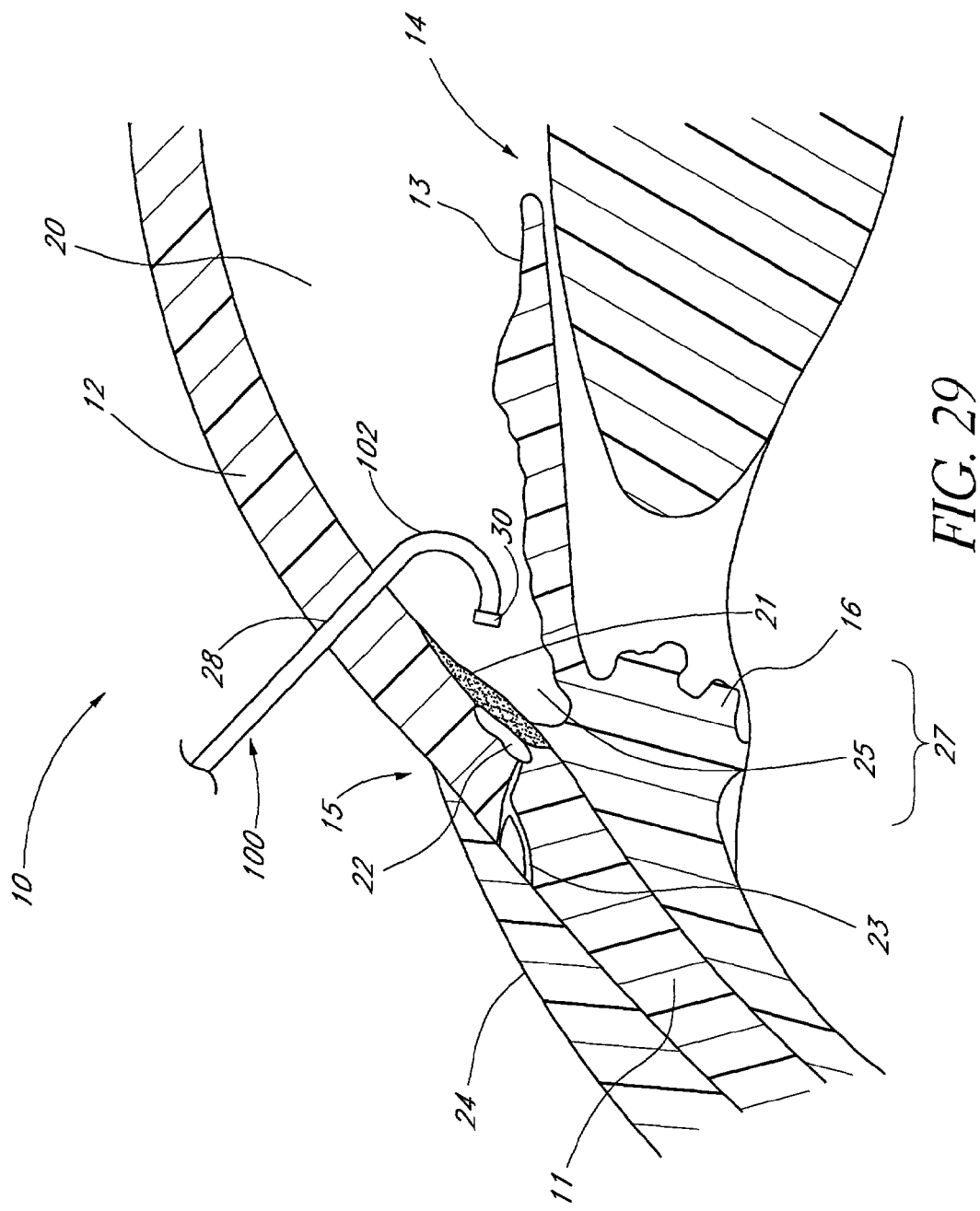
FIG. 29 is a simplified partial view of an eye illustrating the temporal implantation of a glaucoma stent using a delivery apparatus having features and advantages in accordance with one embodiment of the invention.

In many cases, a surgeon works from a temporal incision when performing cataract or goniometry surgery. FIG. 29 illustrates a temporal implant procedure, wherein a delivery apparatus or "applicator" 100 having a curved tip 102 is used to deliver a stent 30 to a temporal side 27 of the eye 10. An incision 28 is made in the cornea 10, as discussed above. The apparatus 100 is then used to introduce the stent 30 through the incision 28 and implant it within the eye 10.

Still referring in particular to FIG. 29, in one embodiment, a similarly curved instrument would be used to make the incision through the trabecular meshwork 21. In other embodiments, a self-trephining stent device 30 may be used to make this incision through the trabecular meshwork 21, as discussed above. The temporal implantation procedure illustrated in FIG. 29 may be employed with the any of the various stent embodiments taught or suggested herein.

Figure 30:
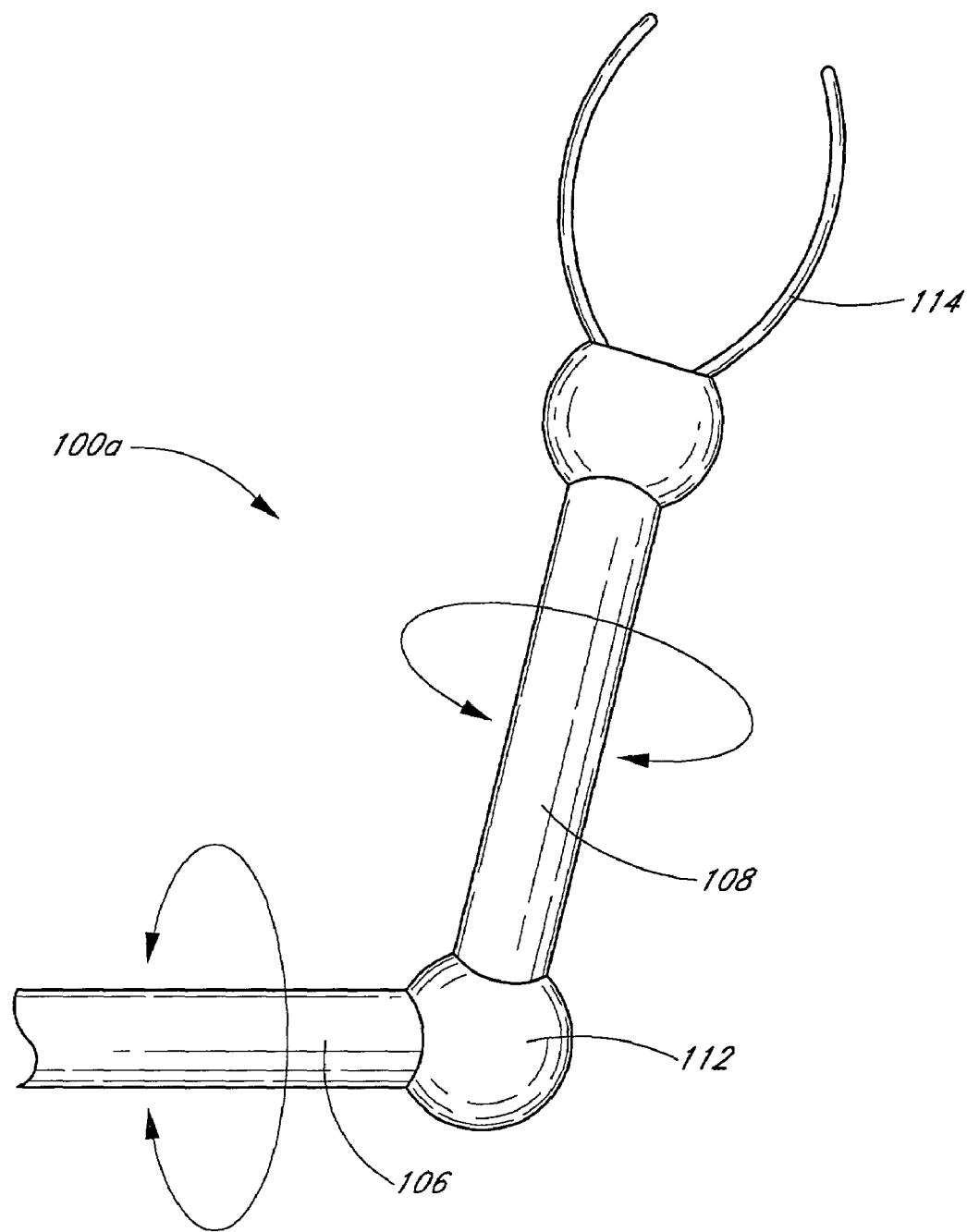
FIG. 30 is an oblique elevational view of an articulating arm stent delivery/retrieval apparatus having features and advantages in accordance with one embodiment of the invention.

FIG. 30 illustrates one embodiment of an apparatus comprising an articulating stent applicator or retrieval device 100a. In this embodiment, a proximal arm 106 is attached to a distal arm 108 at a joint 112. This joint 112 is movable such that an angle formed between the proximal arm 106 and the distal arm 108 can change. One or more claws 114 can extend from the distal arm 108, in the case of a stent retrieval device. Similarly, this articulation mechanism may be used for the trabecular stent applicator, and thus the articulating applicator or retrieval device 100a may be either an applicator for the trabecular stent, a retrieval device, or both, in various embodiments. The embodiment of FIG. 30 may be employed with the any of the various stent embodiments taught or suggested herein.

Figure 31:
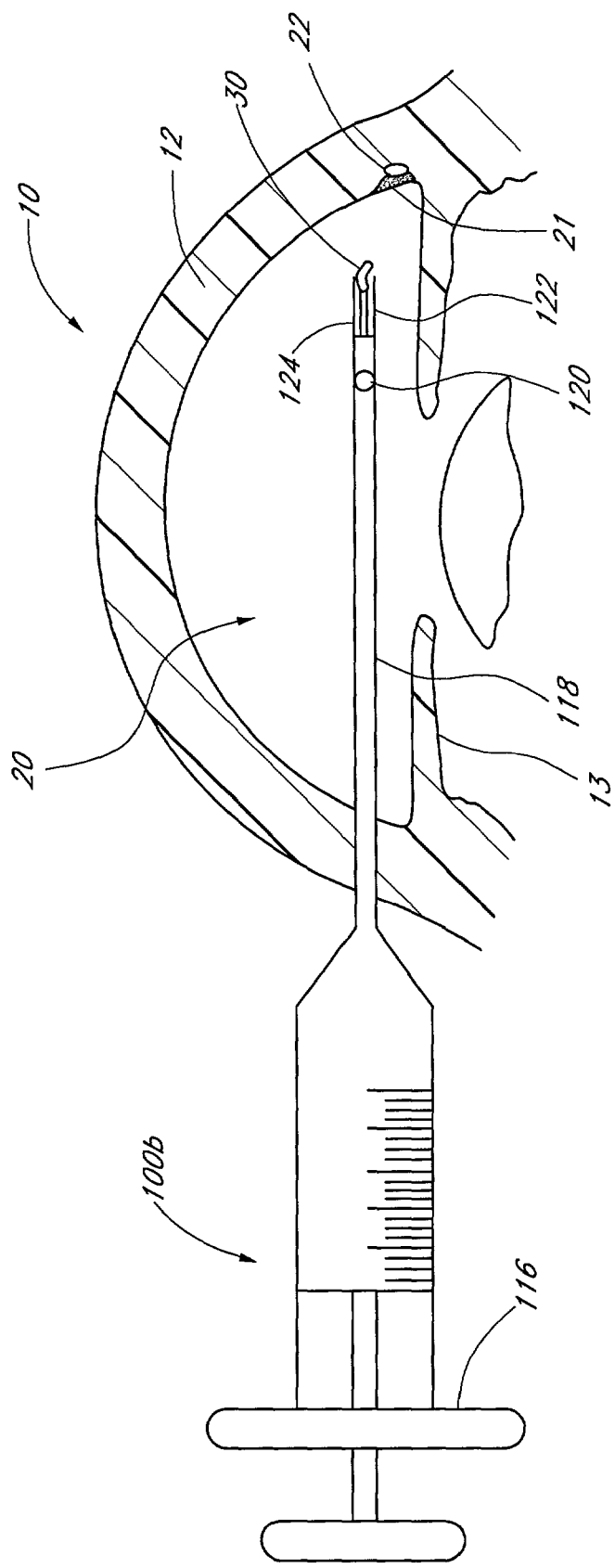
FIG. 31 is a simplified partial view of an eye illustrating the implantation of a glaucoma stent using a delivery apparatus crossing through the eye anterior chamber.

FIG. 31 shows another illustrative method for placing any of the various stent embodiments taught or suggested herein at the implant site within the eye 10. A delivery apparatus 100b generally comprises a syringe portion 116 and a cannula portion 118. The distal section of the cannula 118 has at least one irrigating hole 120 and a distal space 122 for holding the stent device 30. The proximal end 124 of the lumen of the distal space 122 is sealed from the remaining lumen of the cannula portion 118. The delivery apparatus of FIG. 30 may be employed with the any of the various stent embodiments taught or suggested herein.

In one aspect of the invention, a delivery apparatus (or "applicator") is used for placing a trabecular stent through a trabecular meshwork of an eye. Certain embodiments of such a delivery apparatus are disclosed in copending U.S. application Ser. No. 10/101,548 (Inventors: Gregory T. Smedley, Irvine, Calif., Morteza Gharib, Pasadena, Calif., Hosheng Tu, Newport Beach, Calif.; ), filed Mar. 18, 2002, entitled APPLICATOR AND METHODS FOR PLACING A TRABECULAR SHUNT FOR GLAUCOMA TREATMENT, and U.S. Provisional Application No. 60/276,609, filed Mar. 16, 2001, entitled APPLICATOR AND METHODS FOR PLACING A TRABECULAR SHUNT FOR GLAUCOMA TREATMENT, the entire contents of each one of which are hereby incorporated by reference herein.

The stent has an inlet section and an outlet section. The delivery apparatus includes a handpiece, an elongate tip, a holder and an actuator. The handpiece has a distal end and a proximal end. The elongate tip is connected to the distal end of the handpiece. The elongate tip has a distal portion and is configured to be placed through a corneal incision and into an anterior chamber of the eye. The holder is attached to the distal portion of the elongate tip. The holder is configured to hold and release the inlet section of the trabecular stent. The actuator is on the handpiece and actuates the holder to release the inlet section of the trabecular stent from the holder. When the trabecular stent is deployed from the delivery apparatus into the eye, the outlet section is positioned in substantially opposite directions inside Schlemm's canal. In one embodiment, a deployment mechanism within the delivery apparatus includes a push-pull type plunger.

In some embodiments, the holder comprises a clamp. In some embodiments, the apparatus further comprises a spring within the handpiece that is configured to be loaded when the stent is being held by the holder, the spring being at least partially unloaded upon actuating the actuator, allowing for release of the stent from the holder.

In various embodiments, the clamp comprises a plurality of claws configured to exert a clamping force onto the inlet section of the stent. The holder may also comprise a plurality of flanges.

In some embodiments, the distal portion of the elongate tip is made of a flexible material. This can be a flexible wire. The distal portion can have a deflection range, preferably of about 45 degrees from the long axis of the handpiece.

The delivery apparatus can further comprise an irrigation port in the elongate tip.

Some aspects include a method of placing a trabecular stent through a trabecular meshwork of an eye, the stent having an inlet section and an outlet section, including advancing a delivery apparatus holding the trabecular stent through an anterior chamber of the eye and into the trabecular meshwork, placing part of the stent through the trabecular meshwork and into a Schlemm's canal of the eye; and releasing the stent from the delivery apparatus.

In various embodiments, the method includes using a delivery apparatus that comprises a handpiece having a distal end and a proximal end; an elongate tip connected to the distal end of the handpiece, the elongate tip having a distal portion and being configured to be placed through a corneal incision and into an anterior chamber of the eye; a holder attached to the distal portion of the elongate tip, the holder configured to hold and release the inlet section of the trabecular stent; and an actuator on the handpiece that actuates the holder to release the inlet section of the trabecular stent from the holder.

In one aspect, the trabecular stent is removably attached to a delivery apparatus (also known as "applicator"). When the trabecular stent is deployed from the delivery apparatus into the eye, the outlet section is positioned in substantially opposite directions inside Schlemm's canal. In one embodiment, a deployment mechanism within the delivery apparatus includes a push-pull type plunger. In some embodiments, the delivery applicator may be a guidewire, an expandable basket, an inflatable balloon, or the like.

Other Embodiments

Figure 32:
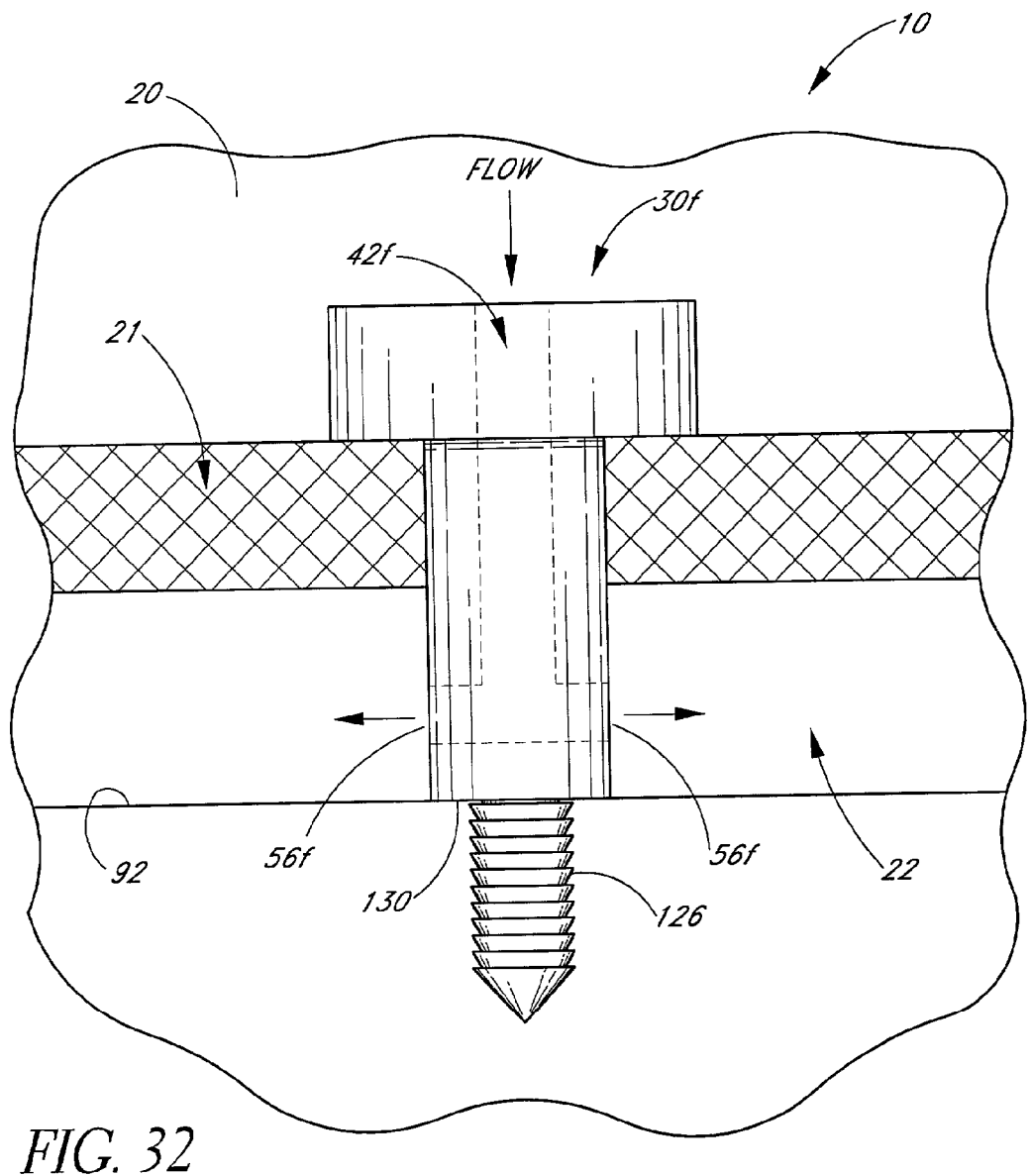
FIG. 32 is a simplified partial view of an eye illustrating the implantation of a glaucoma stent having features and advantages in accordance with one embodiment of the invention.
Figure 33:
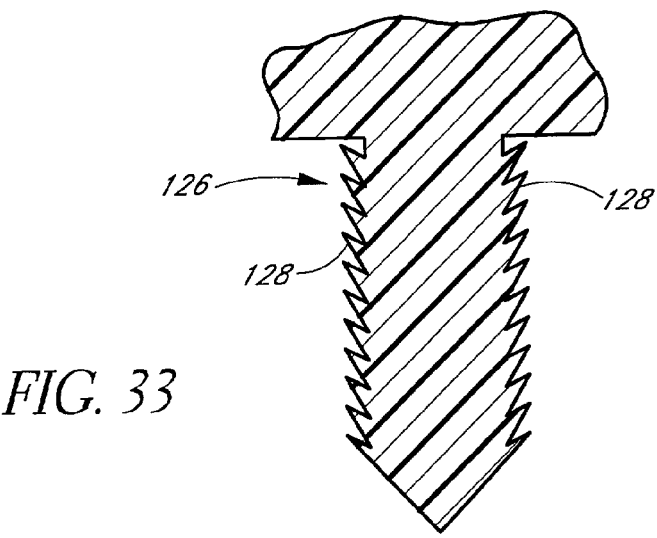
FIG. 33 is a detailed enlarged view of the barbed pin of FIG. 32.

Screw/Barb Anchored Stent:

FIGS. 32 and 33 illustrate a glaucoma stent device 30f having features and advantages in accordance with one embodiment. This embodiment of the trabecular stent 30f includes a barbed or threaded screw-like extension or pin 126 with barbs 128 for anchoring. The barbed pin 126 extends from a distal or base portion 130 of the stent 30f.

In use, the stent 30f (FIG. 32) is advanced through the trabecular meshwork 21 and across Schlemm's canal 22. The barbed (or threaded) extension 126 penetrates into the back wall 92 of Schlemm's canal 22 up to the shoulder or base 130 that then rests on the back wall 92 of the canal 22. The combination of a shoulder 130 and a barbed pin 126 of a particular length limits the penetration depth of the barbed pin 126 to a predetermined or preselected distance. In one embodiment, the length of the pin 126 is about 0.5 mm or less. Advantageously, this barbed configuration provides a secure anchoring of the stent 30f. As discussed above, correct orientation of the stent 30f is ensured by appropriate fiducial marks, indicia or the like and by positioning of the stent in a preloaded applicator.

Referring to FIG. 32, the aqueous flows from the anterior chamber 20, through the lumen 42f, then out through two side-ports 56f to be directed in both directions along Schlemm's canal 22. Alternatively, flow could be directed in only one direction through a single side-port 56f. In other embodiments, more then two outlet ports 56f, for example, six to eight ports (like a pin wheel configuration), may be efficaciously used, as needed or desired.

Still referring to FIG. 32, in one embodiment, the stent 30f is inserted through a previously made incision in the trabecular meshwork 21. In other embodiments, the stent 30f may be combined with any of the blade configurations taught or suggested herein to provide self-trephining capability. In these cases, the incision through the trabecular meshwork 21 is made by the self-trephining stent device which has a blade at its base or proximate to the base.

Figure 34:
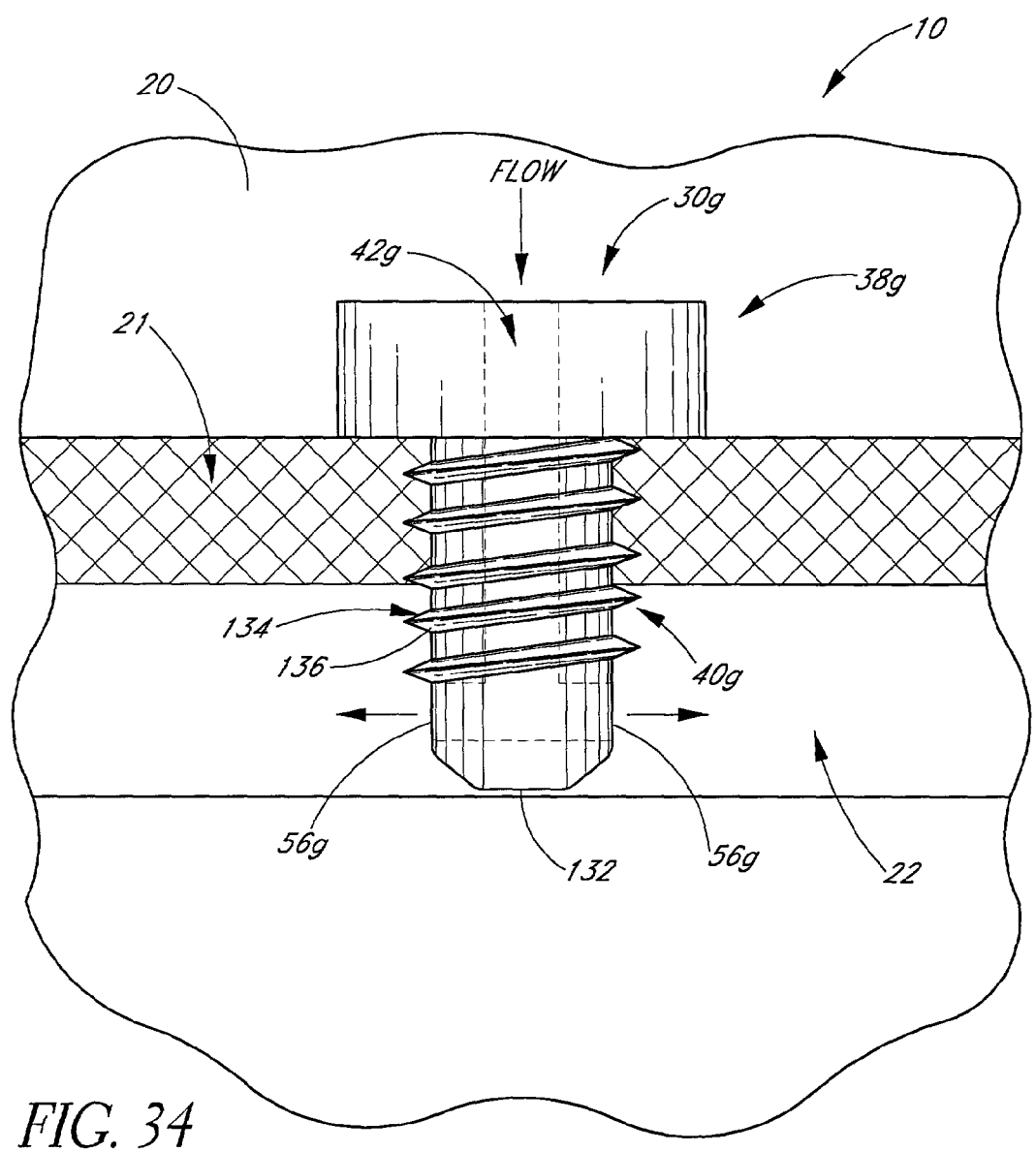
FIG. 34 is a simplified partial view of an eye illustrating the implantation of a glaucoma stent having features and advantages in accordance with one embodiment of the invention.

Deeply Threaded Stent:

FIG. 34 illustrates a glaucoma stent device 30g having features and advantages in accordance with one embodiment. The stent 30g has a head or seat 38g and a shank or main body portion 40g with a base or distal end 132. This embodiment of the trabecular stent 30g includes a deep thread 134 (with threads 136) on the main body 40g of the stent 30g below the head 38g. The threads may or may not extend all the way to the base 132.

In use, the stent 30g (FIG. 34) is advanced through the meshwork 21 through a rotating motion, as with a conventional screw. Advantageously, the deep threads 136 provide retention and stabilization of the stent 30g in the trabecular meshwork 21.

Referring to FIG. 34, the aqueous flows from the anterior chamber 20, through the lumen 42g, then out through two side-ports 56g to be directed in both directions along Schlemm's canal 22. Alternatively, flow could be directed in only one direction through a single side-port 56g. In other embodiments, more then two outlet ports 56g may be efficaciously used, as needed or desired.

One suitable applicator or delivery apparatus for this stent 30g (FIG. 34) includes a preset rotation, for example, via a wound torsion spring or the like. The rotation is initiated by a release trigger on the applicator. A final twist of the applicator by the surgeon and observation of suitable fiducial marks, indicia or the like ensure proper alignment of the side ports 56g with Schlemm's canal 22.

Referring to FIG. 34, in one embodiment, the stent 30g is inserted through a previously made incision in the trabecular meshwork 21. In other embodiments, the stent 30g may be combined with any of the blade configurations taught or suggested herein to provide self-trephining capability. In these cases, the incision through the trabecular meshwork 21 is made by the self-trephining stent device which has a blade at its base or proximate to the base.

Figure 35:
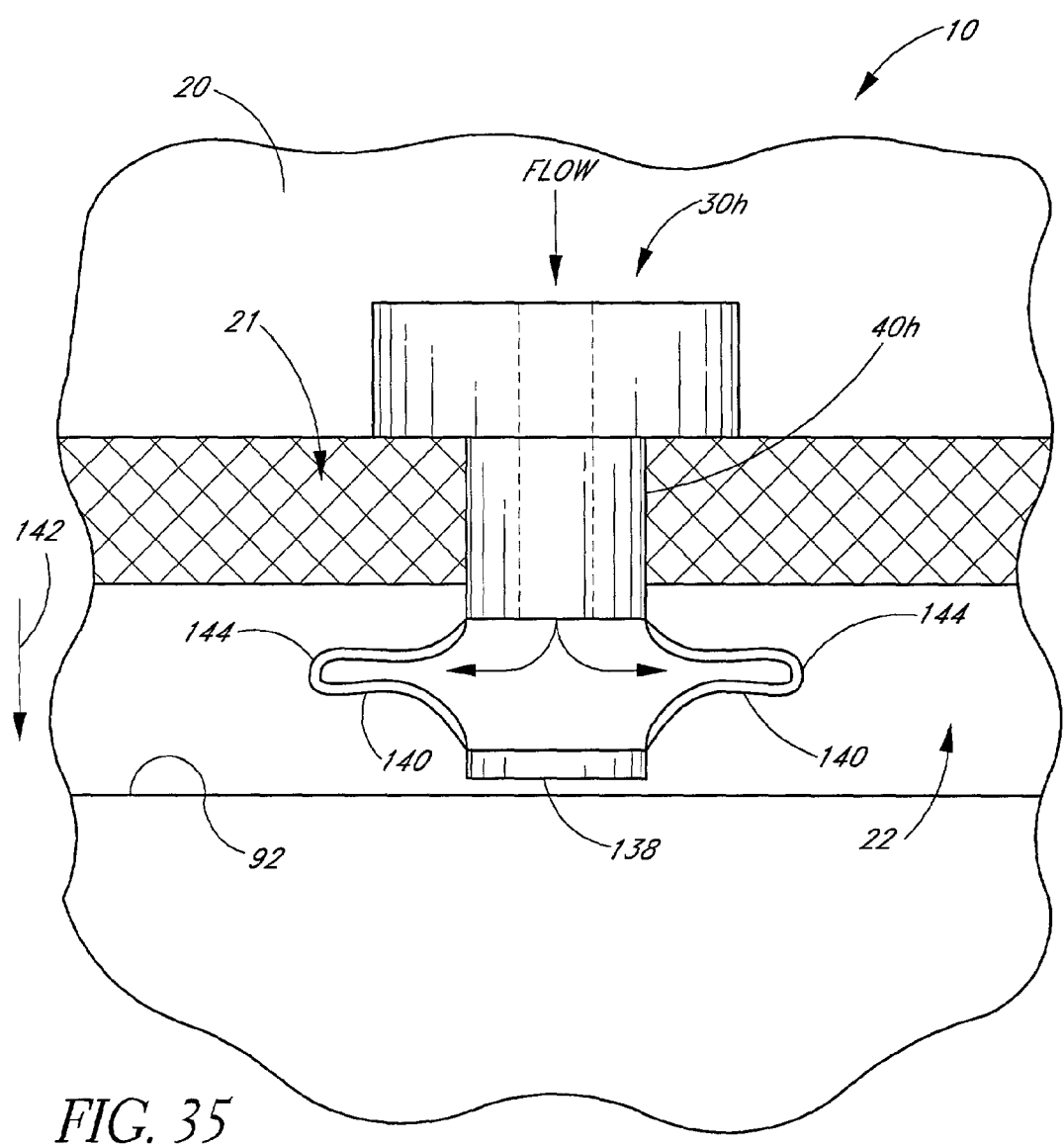
FIG. 35 is a simplified partial view of an eye illustrating the implantation of a glaucoma stent having features and advantages in accordance with one embodiment of the invention.

Rivet Style Stent:

FIG. 35 illustrates a glaucoma stent device 30h having features and advantages in accordance with one embodiment. The stent has a base or distal end 138. This embodiment of the trabecular stent 30h has a pair of flexible ribs 140. In the unused state, the ribs are initially generally straight (that is, extend in the general direction of arrow 142).

Referring to FIG. 35, upon insertion of the stent 30h through the trabecular meshwork 21, the ends 144 of respective ribs 140 of the stent 30h come to rest on the back wall 92 of Schlemm's canal 22. Further advancement of the stent 30h causes the ribs 140 to deform to the bent shape as shown in the drawing of FIG. 35. The ribs 140 are designed to first buckle near the base 138 of the stent 30h. Then the buckling point moves up the ribs 140 as the shank part 40h of the stent 30h is further advanced through the trabecular meshwork 21.

The lumen 42h (FIG. 35) in the stent 30h is a simple straight hole. The aqueous flows from the anterior chamber 20, through the lumen 42h, then out around the ribs 140 to the collector channels further along Schlemm's canal 22 in either direction.

Referring to FIG. 35, in one embodiment, the stent 30h is inserted through a previously made incision in the trabecular meshwork 21. In other embodiments, the stent 30h may be combined with any of the blade configurations taught or suggested herein to provide self-trephining capability. In these cases, the incision through the trabecular meshwork 21 is made by the self-trephining stent device which has a blade at its base or proximate to the base.

Figure 36:
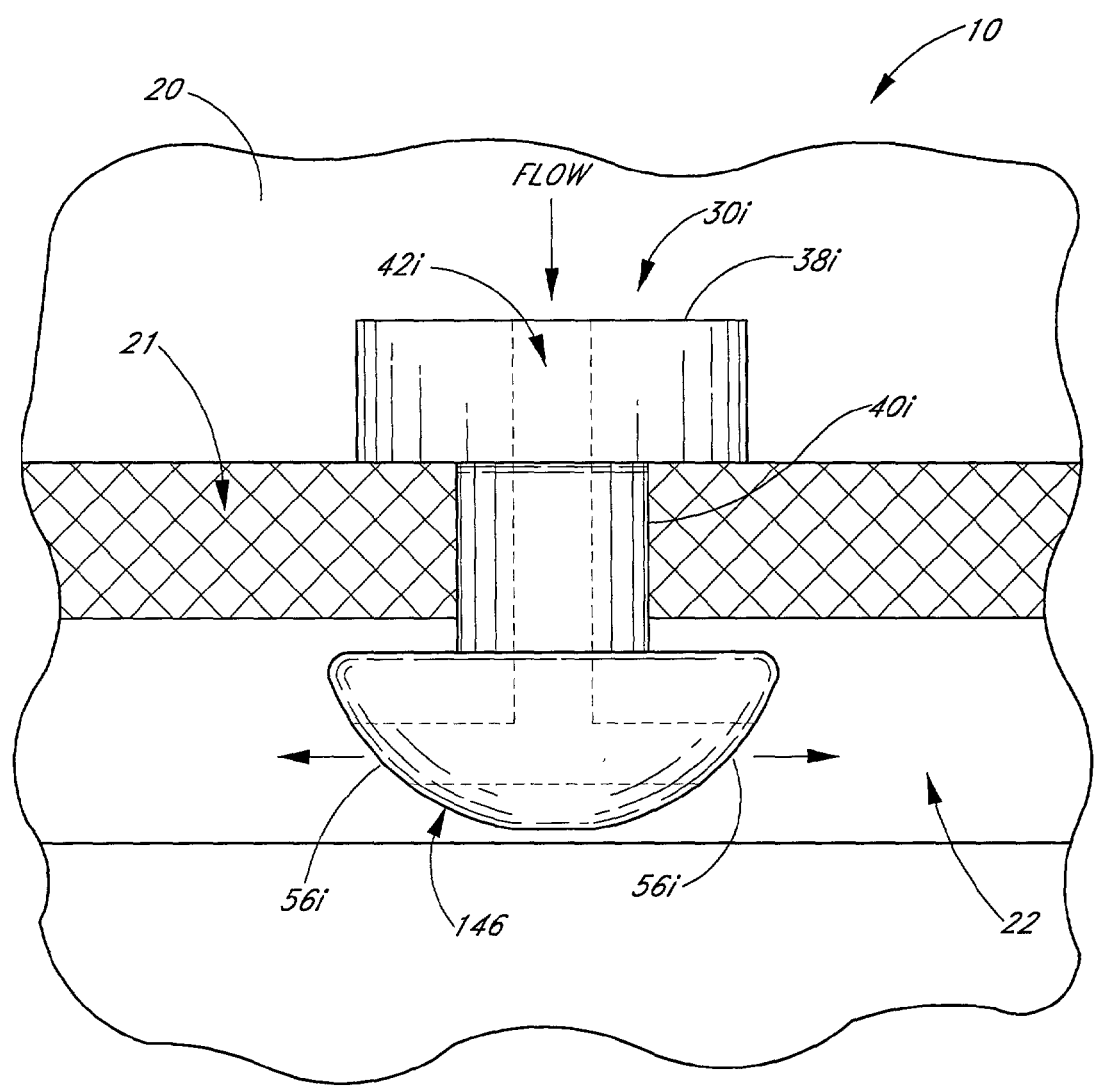
FIG. 36 is a simplified partial view of an eye illustrating the implantation of a glaucoma stent having features and advantages in accordance with one embodiment of the invention.

Grommet Style Stent:

FIG. 36 illustrates a glaucoma stent device 30i having features and advantages in accordance with one embodiment. This embodiment of the trabecular stent 30i includes a head or seat 38i, a tapered base portion 146 and an intermediate narrower waist portion or shank 40i.

In use, the stent 30i (FIG. 36) is advanced through the trabecular meshwork 21 and the base 146 is pushed into Schlemm's canal 22. The stent 30i is pushed slightly further, if necessary, until the meshwork 21 stretched by the tapered base 146 relaxes back and then contracts to engage the smaller diameter portion waist 40i of the stent 30i. Advantageously, the combination of the larger diameter head or seat 38i and base 146 of the stent 30i constrains undesirable stent movement. As discussed above, correct orientation of the stent 30i is ensured by appropriate fiducial marks, indicia or the like and by positioning of the stent in a preloaded applicator.

Referring to FIG. 36, the aqueous flows from the anterior chamber 20, through the lumen 42i, then out through two side-ports 56i to be directed in both directions along Schlemm's canal 22. Alternatively, flow could be directed in only one direction through a single side-port 56i. In other embodiments, more then two outlet ports 56i may be efficaciously used, as needed or desired.

Still referring to FIG. 36, in one embodiment, the stent 30i is inserted through a previously made incision in the trabecular meshwork 21. In other embodiments, the stent 30i may be combined with any of the blade configurations taught or suggested herein to provide self-trephining capability. In these cases, the incision through the trabecular meshwork 21 is made by the self-trephining stent device which has a blade at its base or proximate to the base.

Figure 37:
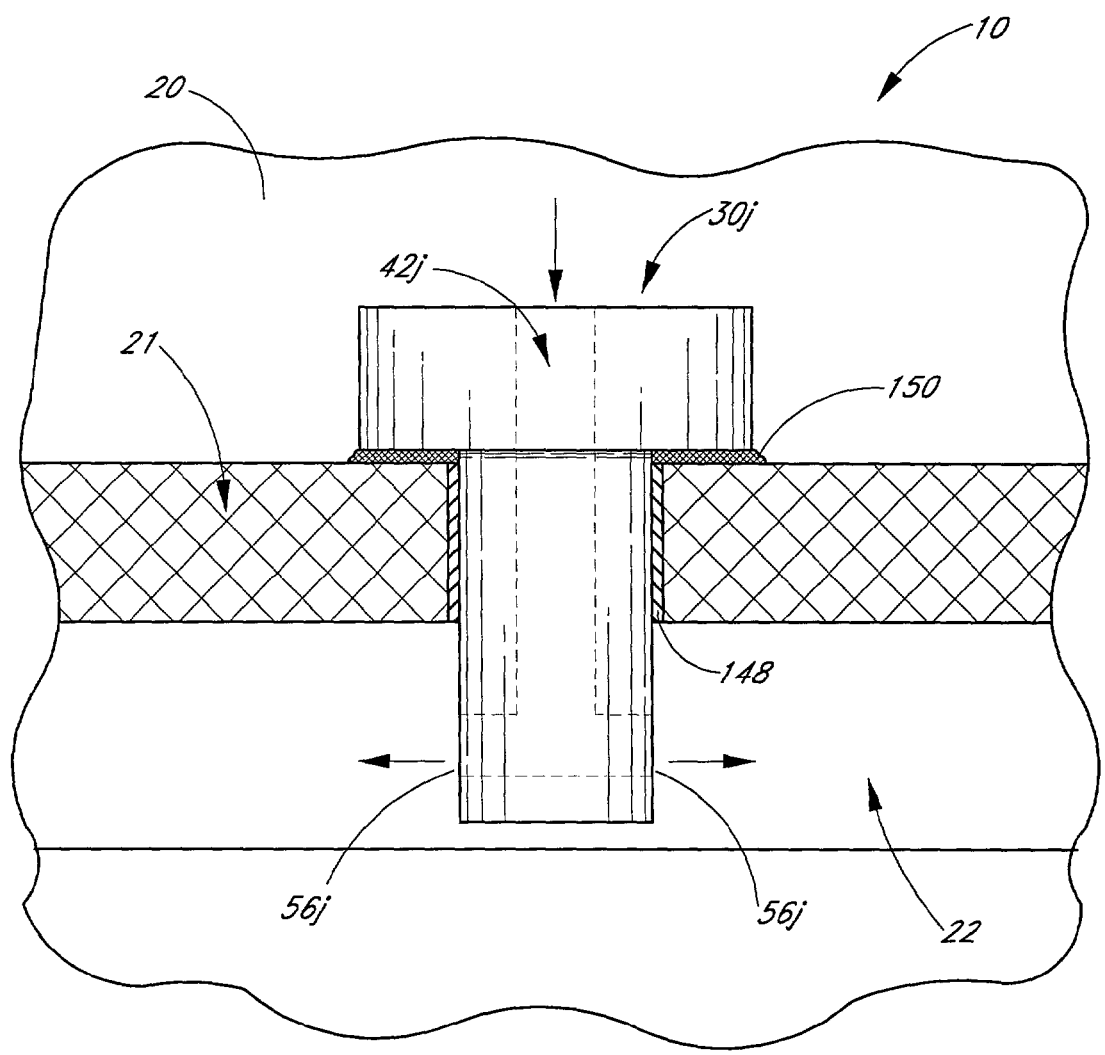
FIG. 37 is a simplified partial view of an eye illustrating the implantation of a glaucoma stent having features and advantages in accordance with one embodiment of the invention.

Biointeractive Stent:

FIG. 37 illustrates a glaucoma stent device 30j having features and advantages in accordance with one embodiment. This embodiment of the trabecular stent 30j utilizes a region of biointeractive material 148 that provides a site for the trabecular meshwork 21 to firmly grip the stent 30j by ingrowth of the tissue into the biointeractive material 148. As shown in FIG. 37, preferably the biointeractive layer 148 is applied to those surfaces of the stent 30j which would abut against or come in contact with the trabecular meshwork 21.

In one embodiment, the biointeractive layer 148 (FIG. 37) may be a region of enhanced porosity with a growth promoting chemical. In one embodiment, a type of bio-glue 150 that dissolves over time is used to hold the stent secure during the time between insertion and sufficient ingrowth for stabilization. As discussed above, correct orientation of the stent 30j is ensured by appropriate fiducial marks, indicia or the like and by positioning of the stent in a preloaded applicator.

Referring to FIG. 37, the aqueous flows from the anterior chamber 20, through the lumen 42j, then out through two side-ports 56j to be directed in both directions along Schlemm's canal 22. Alternatively, flow could be directed in only one direction through a single side-port 56*j*. In other embodiments, more then two outlet ports 56*j* may be efficaciously used, as needed or desired.

Still referring to FIG. 37, in one embodiment, the stent 30*j* is inserted through a previously made incision in the trabecular meshwork 21. In other embodiments, the stent 30*j* may be combined with any of the blade configurations taught or suggested herein to provide self-trephining capability. In these cases, the incision through the trabecular meshwork 21 is made by the self-trephining stent device which has a blade at its base or proximate to the base.

Figure 38:
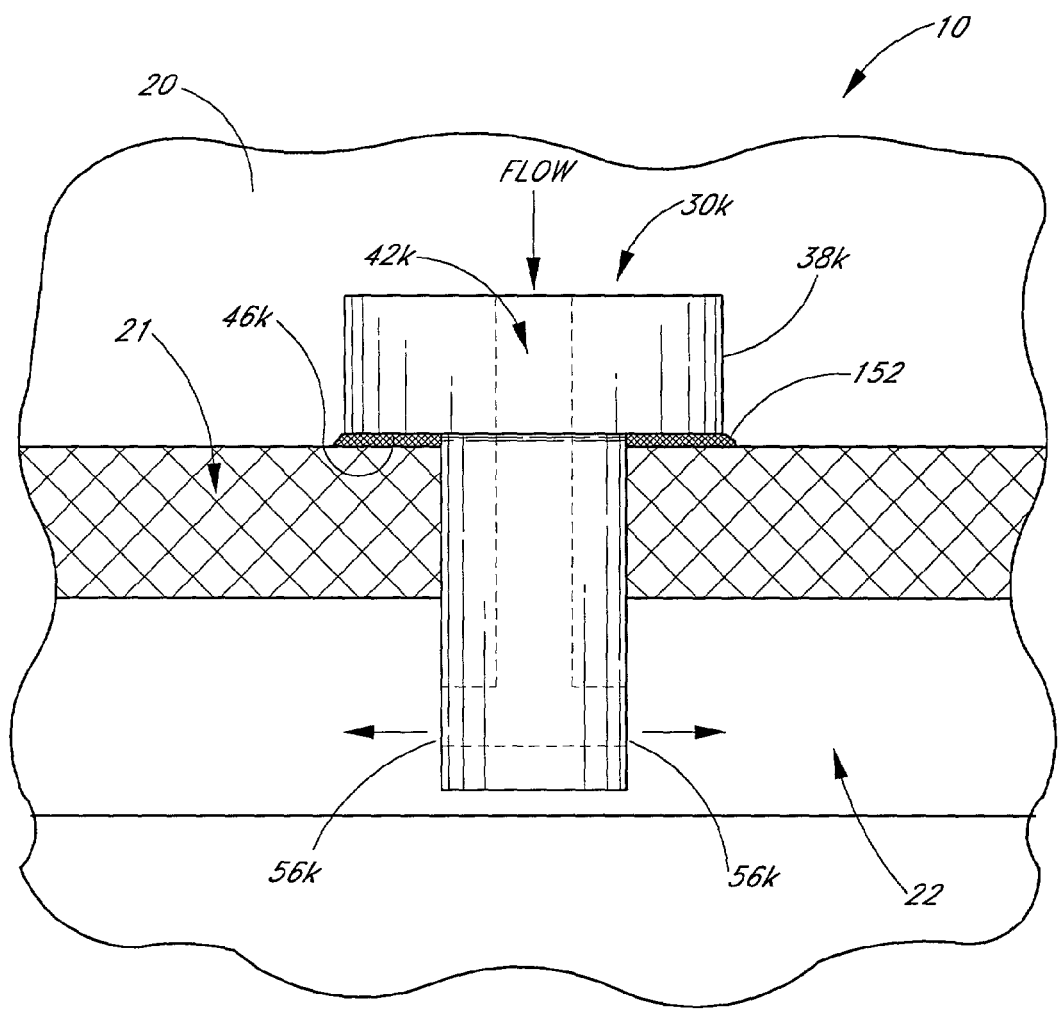
FIG. 38 is a simplified partial view of an eye illustrating the implantation of a glaucoma stent having features and advantages in accordance with one embodiment of the invention.

Glued or Welded Stent:

FIG. 38 illustrates a glaucoma stent device 30*k* having features and advantages in accordance with one embodiment. This embodiment of the trabecular stent 30*k* is secured in place by using a permanent (non-dissolving) bio-glue 152 or a "welding" process (e.g. heat) to form a weld 152. The stent 30*k* has a head or seat 38*k* and a lower surface 46*k*.

The stent 30*k* is advanced through the trabecular meshwork 21 until the head or seat 38*k* comes to rest on the trabecular meshwork 21, that is, the head lower surface 46*k* abuts against the trabecular meshwork 21, and the glue or weld 152 is applied or formed therebetween, as shown in FIG. 38. As discussed above, correct orientation of the stent 30*k* is ensured by appropriate fiducial marks, indicia or the like and by positioning of the stent in a preloaded applicator.

Referring to FIG. 38, the aqueous flows from the anterior chamber 20, through the lumen 42*k*, then out through two side-ports 56*k* to be directed in both directions along Schlemm's canal 22. Alternatively, flow could be directed in only one direction through a single side-port 56*k*. In other embodiments, more then two outlet ports 56*k* may be efficaciously used, as needed or desired.

Still referring to FIG. 38, in one embodiment, the stent 30*k* is inserted through a previously made incision in the trabecular meshwork 21. In other embodiments, the stent 30*k* may be combined with any of the blade configurations taught or suggested herein to provide self-trephining capability. In these cases, the incision through the trabecular meshwork 21 is made by the self-trephining stent device which has a blade at its base or proximate to the base.

Figure 39:
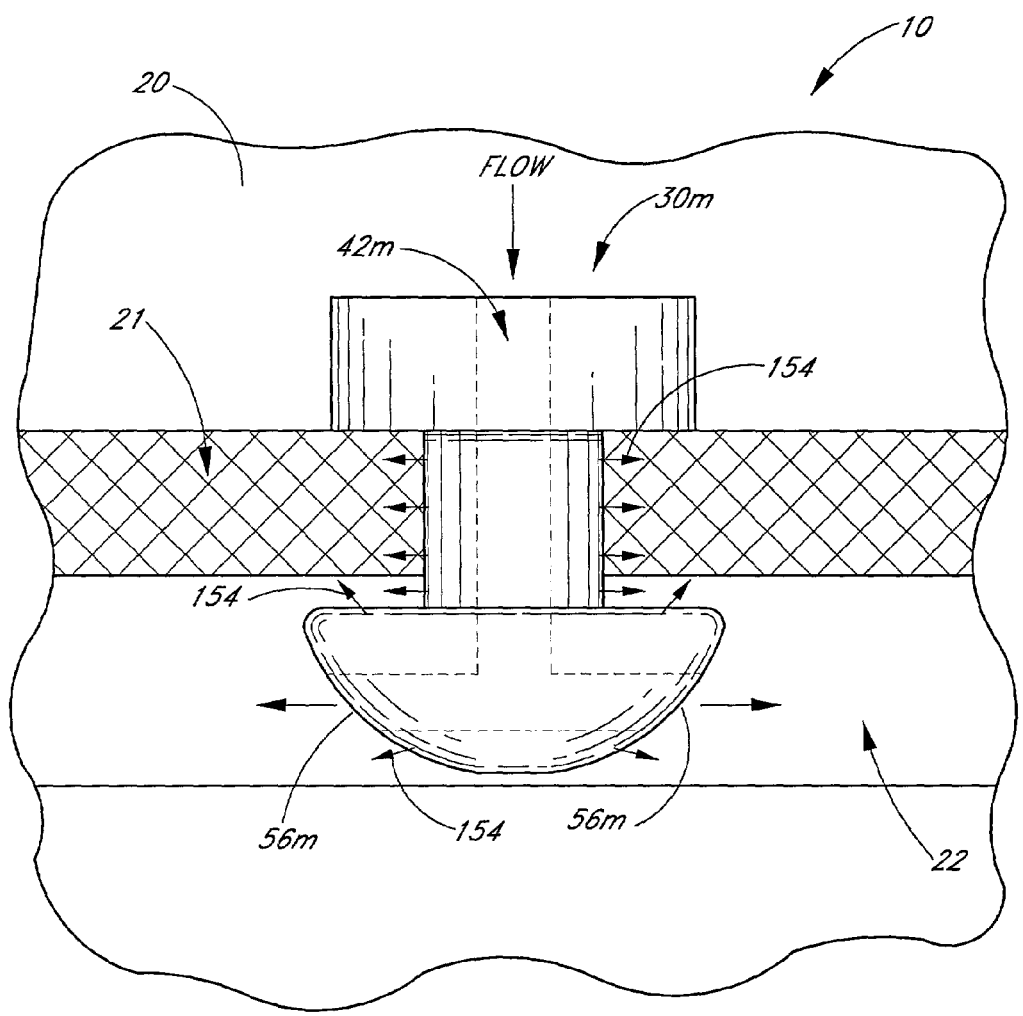
FIG. 39 is a simplified partial view of an eye illustrating the implantation of a glaucoma stent having features and advantages in accordance with one embodiment of the invention.

Hydrophilic Latching Stent:

FIG. 39 illustrates a glaucoma stent device 30*m* having features and advantages in accordance with one embodiment. This embodiment of the trabecular stent 30*m* is fabricated from a hydrophilic material that expands with absorption of water. Desirably, this would enable the device 30*m* to be inserted through a smaller incision in the trabecular meshwork 21. The subsequent expansion (illustrated by the smaller arrows 154) of the stent 30*m* would advantageously enable it to latch in place in the trabecular meshwork 21. As discussed above, correct orientation of the stent 30*m* is ensured by appropriate fiducial marks, indicia or the like and by positioning of the stent in a preloaded applicator.

Referring to FIG. 39, the aqueous flows from the anterior chamber 20, through the lumen 42*m*, then out through two side-ports 56*m* to be directed in both directions along Schlemm's canal 22. Alternatively, flow could be directed in only one direction through a single side-port 56*m*. In other embodiments, more then two outlet ports 56*m* may be efficaciously used, as needed or desired.

Still referring to FIG. 39, in one embodiment, the stent 30*m* is inserted through a previously made incision in the trabecular meshwork 21. In other embodiments, the stent 30*m* may be combined with any of the blade configurations taught or suggested herein to provide self-trephining capability. In these cases, the incision through the trabecular meshwork 21 is made by the self-trephining stent device which has a blade at its base or proximate to the base.

Figure 40:
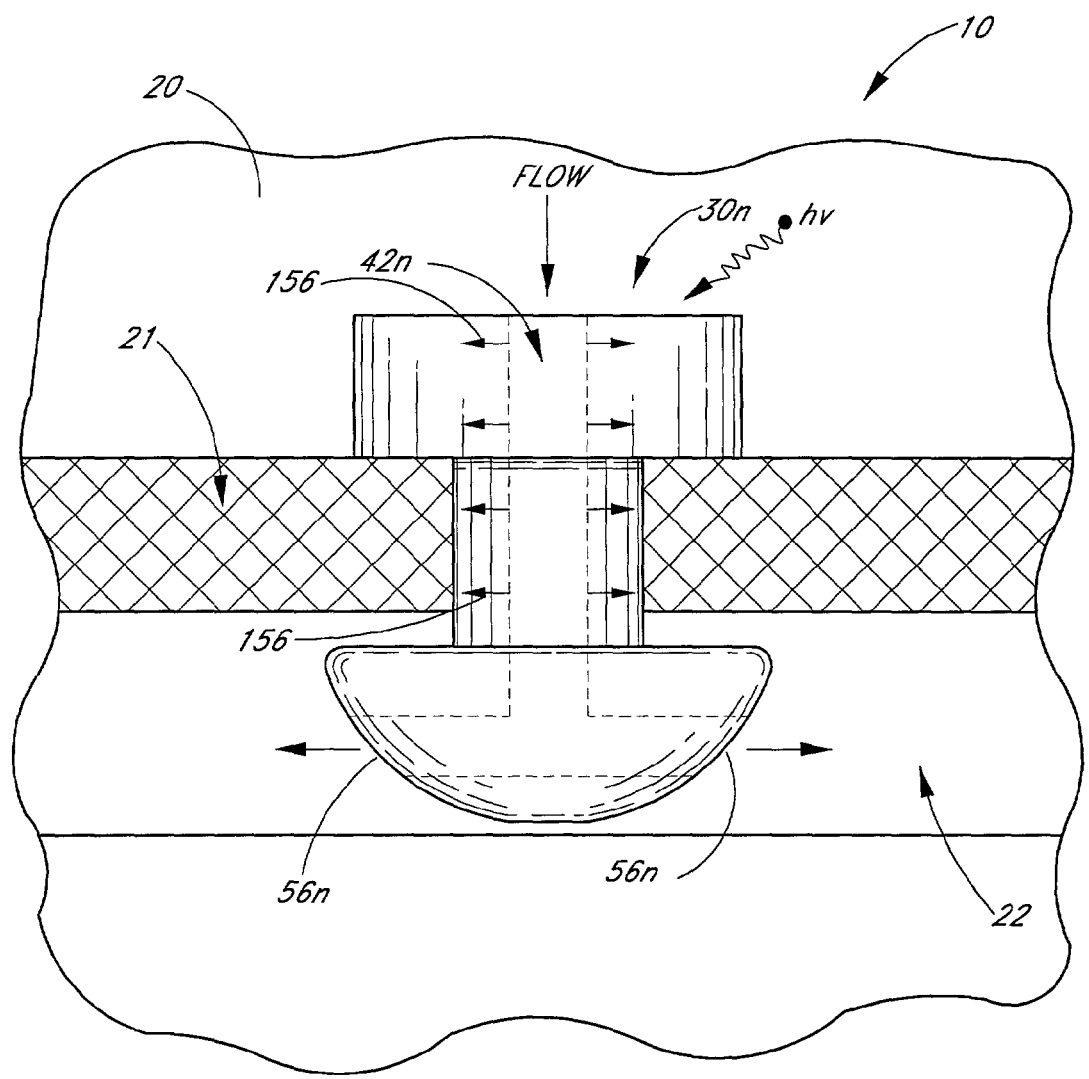
FIG. 40 is a simplified partial view of an eye illustrating the implantation of a glaucoma stent having features and advantages in accordance with one embodiment of the invention.

Photodynamic Stent:

FIG. 40 illustrates a glaucoma stent device 30*n* having features and advantages in accordance with one embodiment. This embodiment of the trabecular stent 30*n* is fabricated from a photodynamic material that expands on exposure to light.

It is commonly known that there is a diurnal variation in the aqueous humor production by the eye—it is higher during the day than it is at night. The lumen 42*n* of the stent 30*n* responds to light entering the cornea during the day by expanding and allowing higher flow of aqueous through the lumen 42*n* and into Schlemm's canal 22. This expansion is generally indicated by the smaller arrows 156 (FIG. 40) which show the lumen 42*n* (and ports) expanding or opening in response to light stimulus. (The light or radiation energy E is generally given by $E=h\nu$, where h is Planck's constant and $\nu$ is the frequency of the light provided.) At night, in darkness, the lumen diameter decreases and reduces the flow allowed through the lumen 42*n*. In one embodiment, an excitation wavelength that is different from that commonly encountered is provided on an as-needed basis to provide higher flow of aqueous to Schlemm's canal 22.

This photodynamic implementation is shown in FIG. 40 for the self-latching style of stent 30*n*, but can be efficaciously used with any of the other stent embodiments, as needed or desired. As discussed above, correct orientation of the stent 30*n* is ensured by appropriate fiducial marks, indicia or the like and by positioning of the stent in a preloaded applicator.

Referring to FIG. 40, the aqueous flows from the anterior chamber 20, through the lumen 42*n*, then out through two side-ports 56*n* to be directed in both directions along Schlemm's canal 22. Alternatively, flow could be directed in only one direction through a single side-port 56*n*. In other embodiments, more then two outlet ports 56*n* may be efficaciously used, as needed or desired.

Still referring to FIG. 40, in one embodiment, the stent 30*n* is inserted through a previously made incision in the trabecular meshwork 21. In other embodiments, the stent 30*n* may be combined with any of the blade configurations taught or suggested herein to provide self-trephining capability. In these cases, the incision through the trabecular meshwork 21 is made by the self-trephining stent device which has a blade at its base or proximate to the base.

Figure 41:
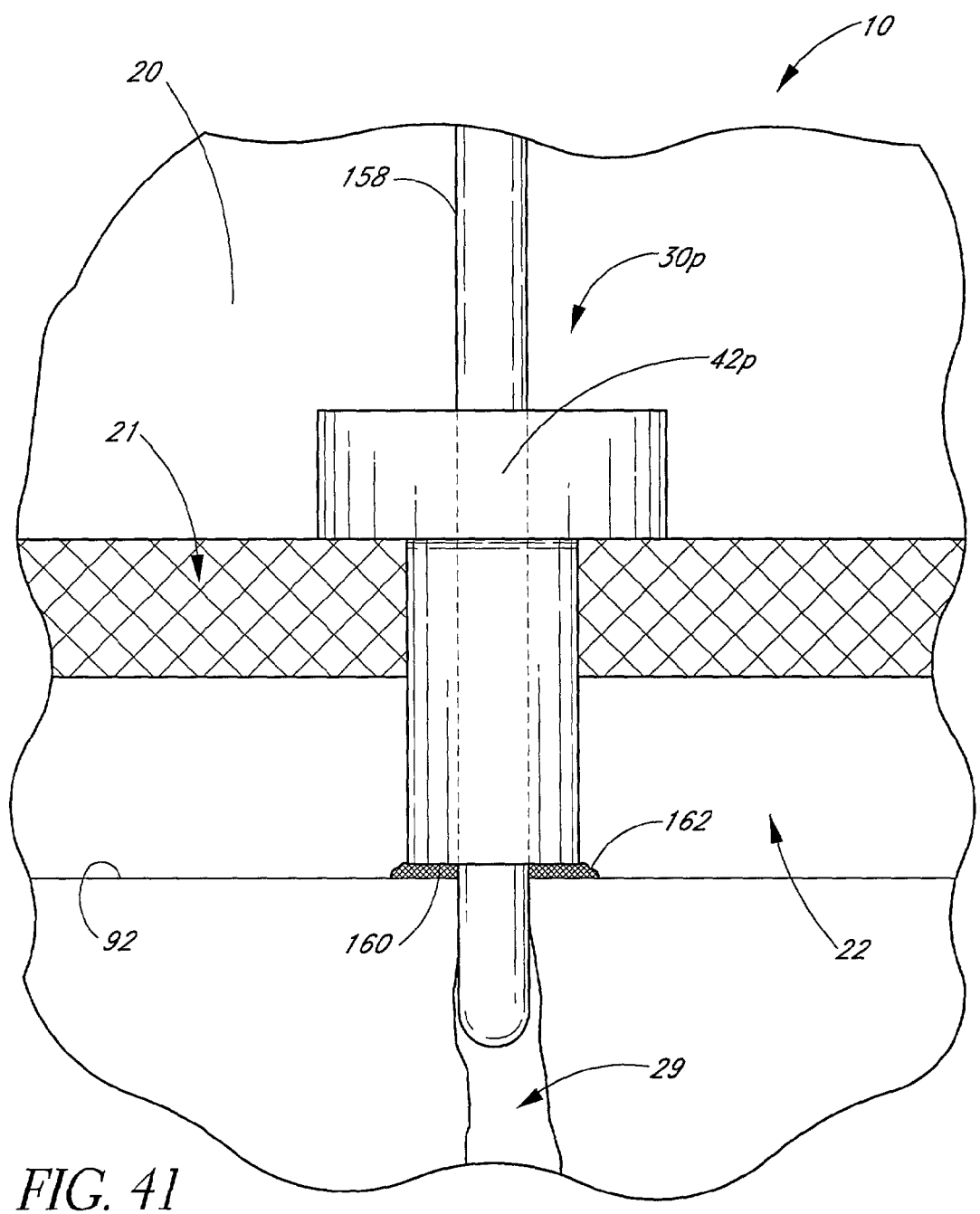
FIG. 41 is a simplified partial view of an eye illustrating the implantation of a glaucoma stent having features and advantages in accordance with one embodiment of the invention.

Collector Channel Alignment Stent:

FIG. 41 illustrates a glaucoma stent device 30*p* having features and advantages in accordance with one embodiment. This figure depicts an embodiment of a stent 30*p* that directs aqueous from the anterior chamber 20 directly into a collector channel 29 which empties into aqueous veins. The stent 30*p* has a base or distal end 160.

In the illustrated embodiment of FIG. 41, a removable alignment pin 158 is utilized to align the stent lumen 42*p* with the collector channel 29. In use, the pin 158 extends through the stent lumen 42*p* and protrudes through the base 160 and extends into the collector channel 29 to center and/or align the stent 30*p* over the collector channel 29. The stent 30*p* is then pressed firmly against the back wall 92 of Schlemm's canal 22. A permanent bio-glue 162 is used between the stent base and the back wall 92 of Schlemm's canal 22 to seat and securely hold the stent 30*p* in place. Once positioned, the pin 158 is withdrawn from the lumen

42p to allow the aqueous to flow directly from the anterior chamber 20 into the collector duct 29. The collector ducts are nominally 20 to 100 micrometers (μm) in diameter and are visualized with a suitable microscopy method (such as ultrasound biomicroscopy (UBM)) or laser imaging to provide guidance for placement of the stent 30p.

Referring to FIG. 41, in one embodiment, the stent 30p is inserted through a previously made incision in the trabecular meshwork 21. In other embodiments, the stent 30p may be combined with any of the blade configurations taught or suggested herein to provide self-trephining capability. In these cases, the incision through the trabecular meshwork 21 is made by the self-trephining stent device which has a blade at its base or proximate to the base.

Figure 42:
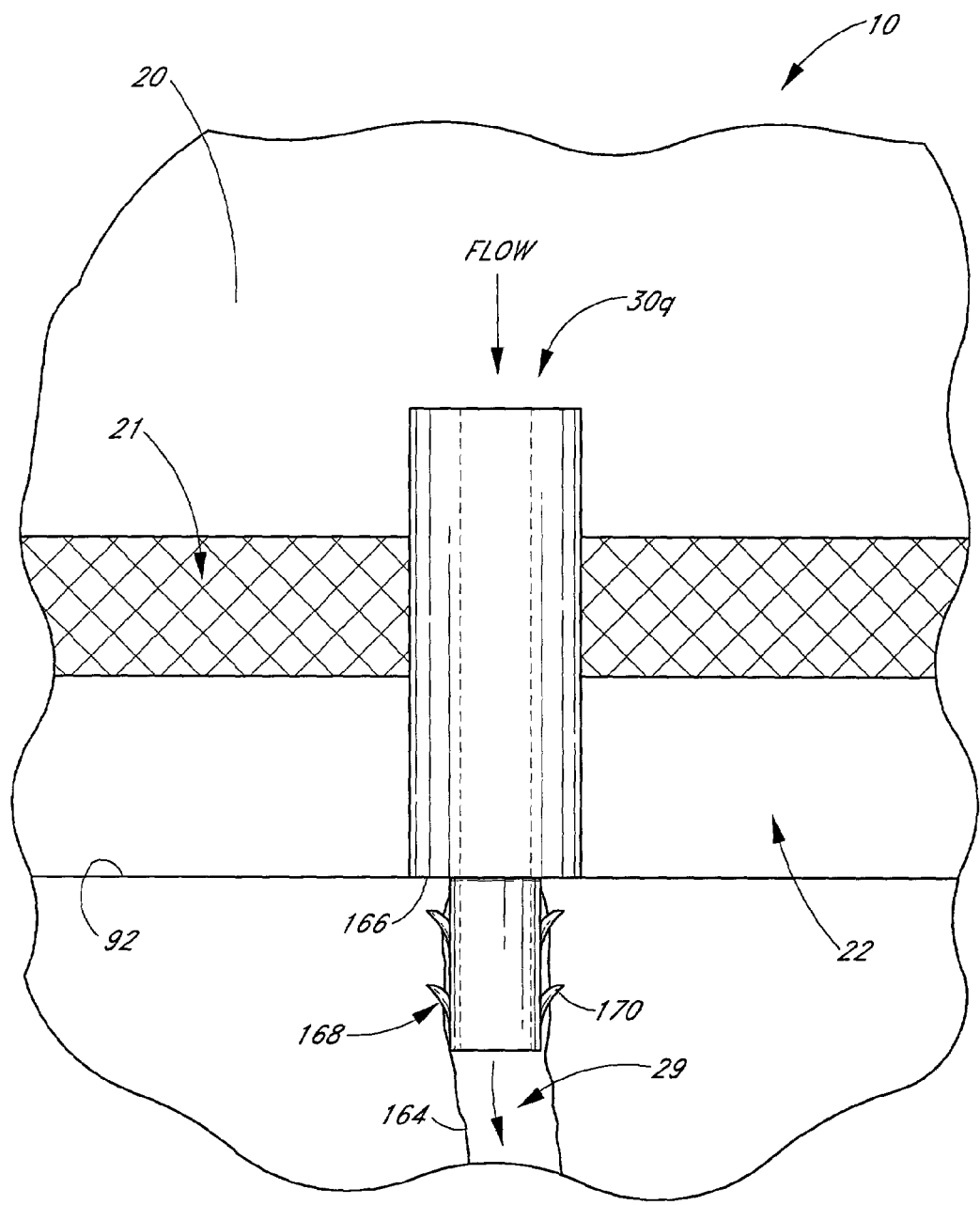
FIG. 42 is a simplified partial view of an eye illustrating the implantation of a glaucoma stent having features and advantages in accordance with one embodiment of the invention.

Barbed Stent (Anterior Chamber to Collector Channel):

FIG. 42 illustrates a glaucoma stent device 30q having features and advantages in accordance with one embodiment. This figure depicts an embodiment of a stent 30q that directs aqueous from the anterior chamber 20 directly into a collector channel 29 which empties into aqueous veins. The stent 30q has a base or distal end 166 and the channel 29 has wall(s) 164.

In the illustrated embodiment of FIG. 42, a barbed, small-diameter extension or pin 168 on the stent base 166 is guided into the collector channel 29 and anchors on the wall(s) 164 of the channel 29. The pin 168 has barbs 170 which advantageously provide anchoring of the stent 30q. The collector ducts 29 are nominally 20 to 100 micrometers (μm) in diameter and are visualized with a suitable microscopy method (such as ultrasound biomicroscopy (UBM)) or laser imaging to provide guidance for placement of the stent.

Referring to FIG. 42, in one embodiment, the stent 30q is inserted through a previously made incision in the trabecular meshwork 21. In other embodiments, the stent 30q may be combined with any of the blade configurations taught or suggested herein to provide self-trephining capability. In these cases, the incision through the trabecular meshwork 21 is made by the self-trephining stent device which has a blade at its base or proximate to the base.

Figure 43:
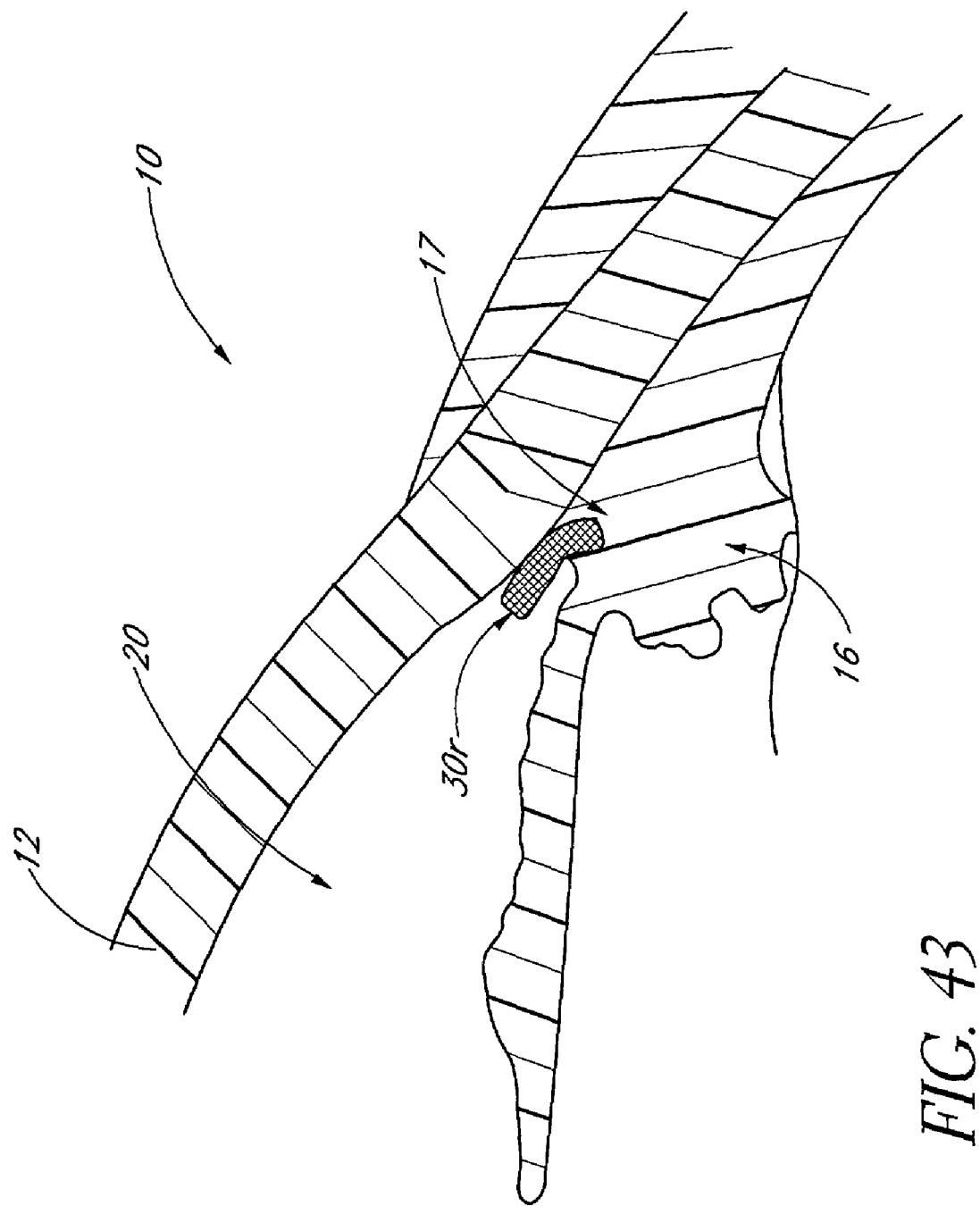
FIG. 43 is a simplified partial view of an eye illustrating the implantation of a valved tube stent device having features and advantages in accordance with one embodiment of the invention.

Valved Tube Stent (Anterior Chamber to Choroid):

FIG. 43 illustrates a valved tube stent device 30r having features and advantages in accordance with one embodiment. This is an embodiment of a stent 30r that provides a channel for flow between the anterior chamber 20 and the highly vascular choroid 17. Clinically, the choroid 17 can be at pressures lower than those desired for the eye 10. Therefore, this stent 30r includes a valve with an opening pressure equal to the desired pressure difference between the choroid 17 and the anterior chamber 10 or a constriction that provide the desired pressure drop.

Figure 44:
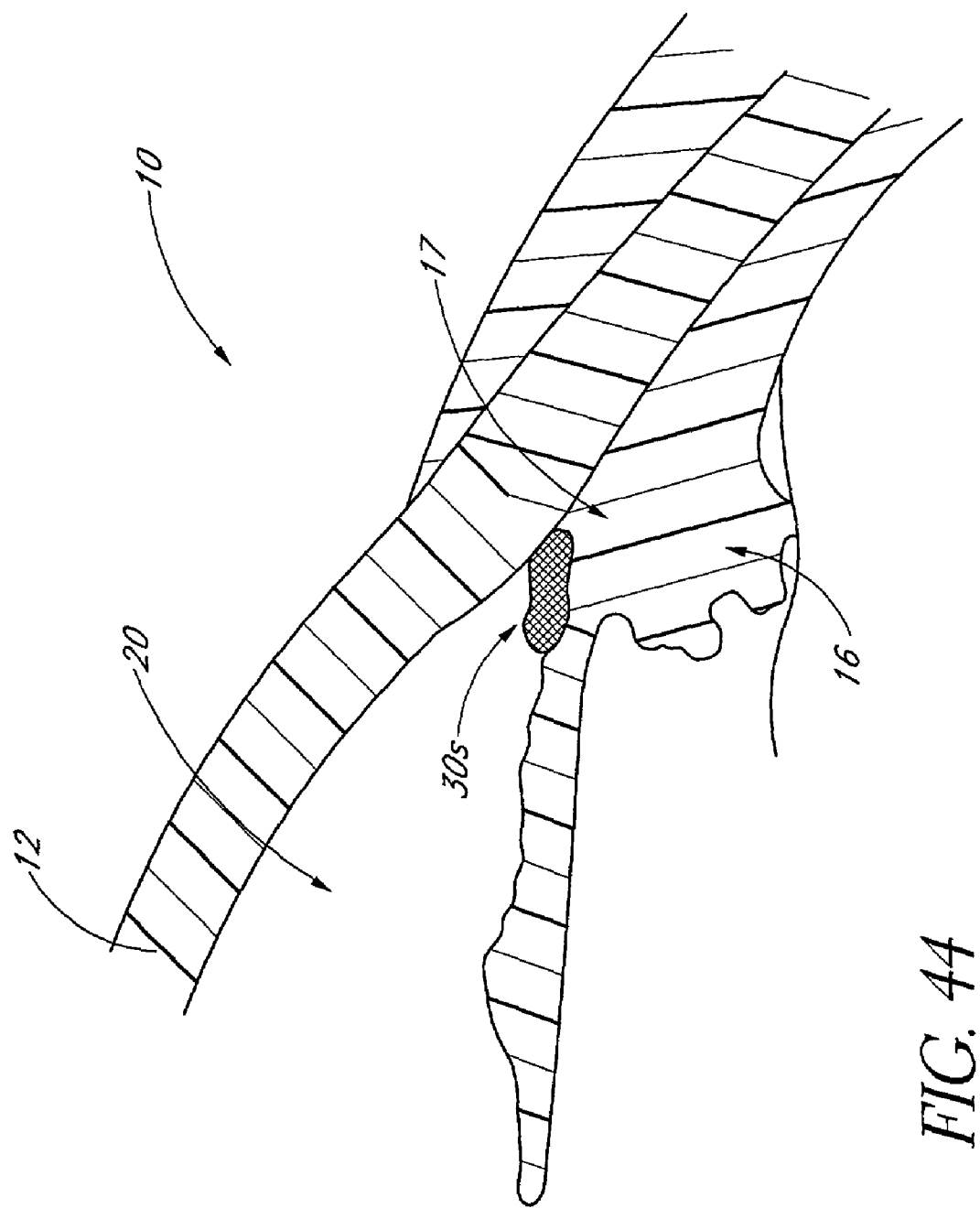
FIG. 44 is a simplified partial view of an eye illustrating the implantation of an osmotic membrane device having features and advantages in accordance with one embodiment of the invention.

Osmotic Membrane (Anterior Chamber to Choroid):

FIG. 44 illustrates a osmotic membrane device 30s having features and advantages in accordance with one embodiment. This embodiment provides a channel for flow between the anterior chamber 20 and the highly vascular choroid 17. The osmotic membrane 30s is used to replace a portion of the endothelial layer of the choroid 17. Since the choroid 17 is highly vascular with blood vessels, the concentration of water on the choroid side is lower than in the anterior chamber 20 of the eye 10. Therefore, the osmotic gradient drives water from the anterior chamber 20 into the choroid 17.

Clinically, the choroid 17 (FIG. 44) can be at pressures lower than those desired for the eye 10. Therefore, desirably, both osmotic pressure and the physical pressure gradient are in favor of flow into the choroid 17. Flow control is provided by proper sizing of the area of the membrane,—the larger the membrane area is the larger the flow rate will be. This advantageously enables tailoring to tune the flow to the desired physiological rates.

Figure 45:
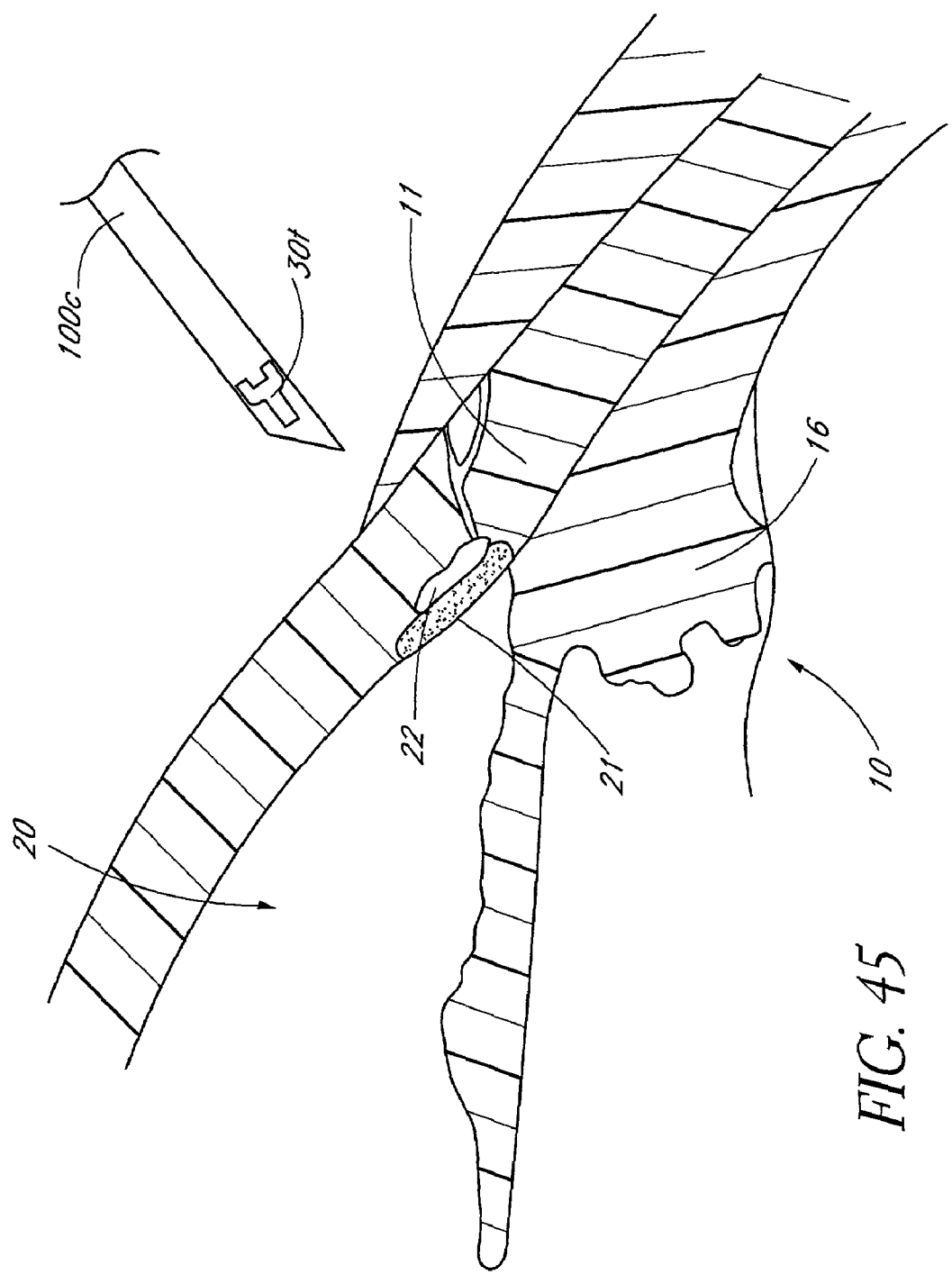
FIG. 45 is a simplified partial view of an eye illustrating the implantation of a glaucoma stent using ab externo procedure having features and advantages in accordance with one embodiment of the invention.

Ab Externo Insertion of Stent via Small Puncture:

FIG. 45 illustrates the implantation of a stent 30t using an ab externo procedure having features and advantages in accordance with one embodiment. In the ab externo procedure of FIG. 45, the stent 30t is inserted into Schlemm's canal 21 with the aid of an applicator or delivery apparatus 100c that creates a small puncture into the eye 10 from outside.

Referring to FIG. 45, the stent 30t is housed in the applicator 100c, and pushed out of the applicator 100c once the applicator tip is in position within the trabecular meshwork 21. Since the tissue surrounding the trabecular meshwork 21 is optically opaque, an imaging technique, such as ultrasound biomicroscopy (UBM) or a laser imaging technique, is utilized. The imaging provides guidance for the insertion of the applicator tip and the deployment of the stent 30t. This technique can be used with a large variety of stent embodiments with slight modifications since the trabecular meshwork 21 is punctured from the scleral side rather than the anterior chamber side in the ab externo insertion.

Figure 46:
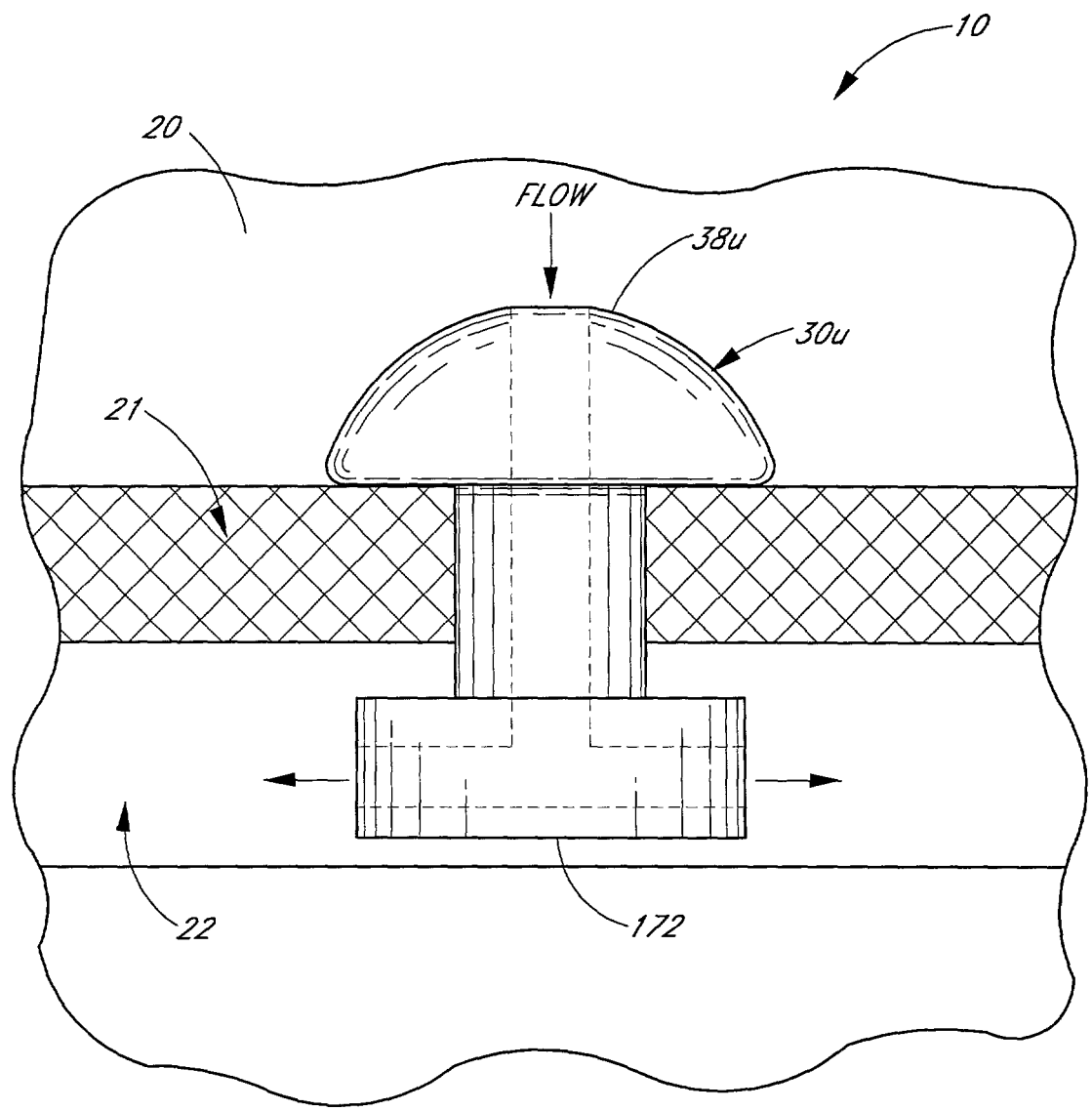
FIG. 46 is a simplified partial view of an eye illustrating the implantation of a glaucoma stent having features and advantages in accordance with a modified embodiment of the invention.

FIG. 46 a glaucoma stent device 30u having features and advantages in accordance with a modified embodiment. This grommet-style stent 30u for ab externo insertion is a modification of the embodiment of FIG. 36. In the embodiment of FIG. 46, the upper part or head 38u is tapered while the lower part or base 172 is flat, as opposed to the embodiment of FIG. 36. The stent 30u is inserted from the outside of the eye 10 through a puncture in the sclera. Many of the other embodiments of stents taught or suggested herein can be modified for similar implantation.

This ultra microscopic device 30u (FIG. 46) can be used with (1) a targeting Lasik-type laser, or with (2) contact on eyes or with (3) combined ultrasound microscope or (4) other device insertor handpiece.

Figure 47:
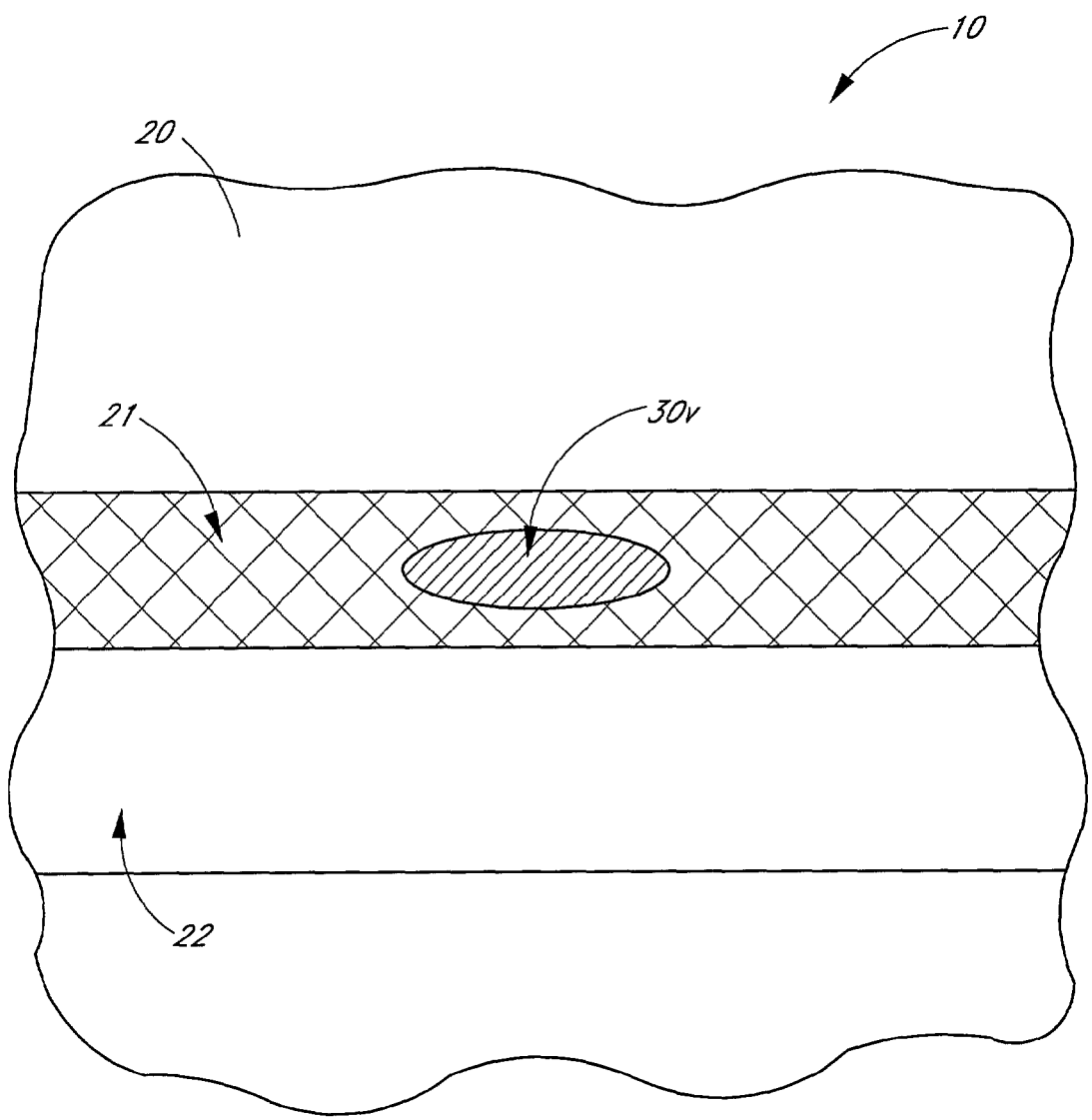
FIG. 47 is a simplified partial view of an eye illustrating the implantation of a drug release implant having features and advantages in accordance with one embodiment of the invention.

Targeted Drug Delivery to the Trabecular Meshwork:

FIG. 47 illustrates a targeted drug delivery implant 30v having features and advantages in accordance with one embodiment. This drawing is a depiction of a targeted drug delivery concept. The slow release implant 30v is implanted within the trabecular meshwork 21.

A drug that is designed to target the trabecular meshwork 21 to increase its porosity, or improve the active transport across the endothelial layer of Schlemm's canal 22 can be stored in this small implant 30v (FIG. 47). Advantageously, slow release of the drug promotes the desired physiology at minimal dosage levels since the drug is released into the very structure that it is designed to modify.

While the components and techniques of the invention have been described with a certain degree of particularity, it is manifest that many changes may be made in the specific designs, constructions and methodology herein above described without departing from the spirit and scope of this disclosure. It should be understood that the invention is not limited to the embodiments set forth herein for purposes of exemplification, but is to be defined only by a fair reading of the appended claims, including the full range of equivalency to which each element thereof is entitled.

What is claimed is:

1. A stent for implantation in an eye and for reducing intraocular pressure, comprising:

a stent body having an inlet end and an outlet end, the stent body configured to extend through the eye such that the inlet end resides in the anterior chamber of the eye and the outlet end resides in Schlemm's canal of the eye;

wherein the outlet end of the stent body comprises a cutting member, the cutting member configured to make an incision in the trabecular meshwork of the eye for receiving at least a portion of said stent body; and wherein the stent body is angulated.

2. The stent of claim 1, wherein the stent body is substantially L-shaped.

3. A cutting glaucoma stent for implantation in an eye and for reducing intraocular pressure in an eye, comprising:

a shank adapted to extend through a trabecular meshwork of the eye; and a lumen extending through said shank and having at least one inlet port and at least one outlet port; and an outflow member extending from a first end of said shank and comprising a cutting tip at a distal end of said outflow member that is configured to make an incision in the trabecular meshwork;

wherein the stent is configured to be placed in the eye such that the outflow member resides in a Schlemm's canal of the eye, and a second end of said shank resides in the anterior chamber;

wherein the stent is angulated.

4. The stent of claim 3, wherein the stent is substantially L-shaped.

5. An apparatus for implantation in an eye and for treating glaucoma, comprising:

an angulated implant shaped and sized such that, in an installed position, the implant conveys fluid from the anterior chamber to Schlemm's canal of an eye, said implant having an inlet portion and an outlet portion, said outlet portion having a cutting portion disposed to cut an implant insertion channel through eye tissue and into Schlemm's canal as the implant is advanced from the anterior chamber of the eye and placed into said installed position.

6. The apparatus of claim 5, wherein the implant is substantially L-shaped.

7. A method of implanting an implant in an eye, said implant being angulated and having an inlet portion in fluid communication with an outlet portion, said outlet portion having a distal blade, the method comprising:

advancing said blade at least partially through the trabecular meshwork of the eye to cut the trabecular meshwork and form an incision therein; and passing at least a portion of said implant through the incision;

positioning the implant such that the inlet portion of the implant is in the anterior chamber of the eye, and the outlet portion of the implant is in Schlemm's canal of said eye.

8. The method of claim 7, wherein the implant is substantially L-shaped.

9. The method of claim 7, wherein outlet portion has a curved surface that forms a trough.

10. An stent for reducing intraocular pressure, comprising:

a stent body comprising a tubular inlet end portion and an open-faced outlet end, the stent body configured to extend through the eye such that the inlet end portion resides in the anterior chamber of the eye and the outlet end resides in Schlemm's canal of the eye; and said outlet end comprising a cutting edge having a substantially semi-circular shape when viewed from the outlet end of the stent body.

* * * * *